US008192841B2

(12) United States Patent
Amundson et al.

(10) Patent No.: US 8,192,841 B2
(45) Date of Patent: Jun. 5, 2012

(54) MICROENCAPSULATED DELIVERY VEHICLE HAVING AN AQUEOUS CORE

(75) Inventors: John David Amundson, Greenville, WI (US); William A. Hendrickson, Stillwater, MN (US); David J. Drath, Lakeland, MN (US); Christopher J. Rueb, Saint Paul, MN (US); John Michael Finney, Eden Prairie, MN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1128 days.

(21) Appl. No.: 11/610,980

(22) Filed: Dec. 14, 2006

(65) Prior Publication Data
US 2008/0145426 A1 Jun. 19, 2008

(51) Int. Cl.
*B32B 5/16* (2006.01)
(52) U.S. Cl. .............. 428/402; 428/402.2; 428/402.24
(58) Field of Classification Search ............... 428/40.2, 428/402.2, 402.24, 402.21, 402.22, 402
See application file for complete search history.

(56) References Cited

U.S. PATENT DOCUMENTS

| | | |
|---|---|---|
| 1,312,449 A | 8/1919 | Lundberg |
| 2,766,478 A | 10/1956 | Raley, Jr. et al. |
| 2,789,725 A | 4/1957 | Carper |
| 3,016,308 A | 1/1962 | Macaulay |
| 3,084,664 A | 4/1963 | Solomon et al. |
| 3,175,558 A | 3/1965 | Caillonette et al. |
| 3,199,490 A | 8/1965 | Karlik |
| 3,261,347 A | 7/1966 | Sherman |
| 3,310,353 A | 3/1967 | Cordis |
| 3,363,604 A | 1/1968 | Pschibul |
| 3,388,953 A | 6/1968 | Browning |
| 3,429,827 A | 2/1969 | Ruus |
| 3,441,353 A | 4/1969 | Claff |
| 3,464,413 A | 9/1969 | Goldfarb et al. |
| 3,472,675 A | 10/1969 | Gordon et al. |
| 3,516,941 A | 6/1970 | Matson |
| 3,585,982 A | 6/1971 | Hollinshead |
| 3,638,786 A | 2/1972 | Borecki et al. |
| 3,674,176 A | 7/1972 | Sagi |
| 3,676,190 A | 7/1972 | Lander et al. |
| 3,691,090 A | 9/1972 | Kitajima et al. |
| 3,691,270 A | 9/1972 | Charle et al. |
| 3,707,945 A | 1/1973 | Boone |
| 3,738,857 A | 6/1973 | Brockett et al. |
| 3,756,483 A | 9/1973 | Schraeder |
| 3,804,061 A | 4/1974 | Cassar et al. |
| 3,839,220 A | 10/1974 | Barchas |

(Continued)

FOREIGN PATENT DOCUMENTS
CA 2346223 A 8/2001
(Continued)

OTHER PUBLICATIONS

International Search Report and Written Opinion from PCT/IB2007/051684, dated Nov. 27, 2007.

(Continued)

*Primary Examiner* — Matthew Matzek
(74) *Attorney, Agent, or Firm* — Armstrong Teasdale LLP

(57) ABSTRACT

Microencapsulated delivery vehicles comprising an active agent are disclosed. The microencapsulated delivery vehicles may be introduced into products such that, upon activation, the product provides a functional benefit to a substrate, such as a user's skin.

20 Claims, 2 Drawing Sheets

U.S. PATENT DOCUMENTS

| | | |
|---|---|---|
| 3,849,241 A | 11/1974 | Butin et al. |
| 3,854,624 A | 12/1974 | Canci |
| 3,862,715 A | 1/1975 | Remenyik |
| 3,865,271 A | 2/1975 | Gold |
| 3,889,804 A | 6/1975 | Ravich |
| 3,936,573 A | 2/1976 | Brockett |
| 3,947,571 A | 3/1976 | Murphy et al. |
| 3,980,203 A | 9/1976 | Dearling |
| 3,982,659 A | 9/1976 | Ross |
| 3,994,417 A | 11/1976 | Boedecker |
| 4,004,711 A | 1/1977 | Ravich |
| 4,036,301 A | 7/1977 | Powers et al. |
| 4,041,900 A | 8/1977 | Charles |
| 4,077,390 A | 3/1978 | Stanley et al. |
| 4,088,751 A | 5/1978 | Kenkare et al. |
| 4,100,324 A | 7/1978 | Anderson et al. |
| 4,106,433 A | 8/1978 | Fernando et al. |
| 4,106,616 A | 8/1978 | Boone |
| 4,132,771 A | 1/1979 | Schreiber et al. |
| 4,159,316 A | 6/1979 | Januszewski et al. |
| 4,187,287 A | 2/1980 | Schreiber et al. |
| 4,362,715 A | 12/1982 | Strianse et al. |
| 4,375,448 A | 3/1983 | Appel et al. |
| 4,379,143 A | 4/1983 | Sherry et al. |
| 4,407,957 A | 10/1983 | Lim |
| 4,436,224 A | 3/1984 | McInery |
| 4,460,563 A | 7/1984 | Calanchi |
| 4,504,402 A | 3/1985 | Chen |
| 4,505,953 A | 3/1985 | Chen |
| 4,513,053 A | 4/1985 | Chen |
| 4,514,461 A | 4/1985 | Woo |
| 4,516,564 A | 5/1985 | Koiso et al. |
| 4,568,559 A | 2/1986 | Nuwayser et al. |
| 4,598,664 A | 7/1986 | Hamlin |
| 4,620,502 A | 11/1986 | Kimble |
| 4,626,550 A | 12/1986 | Hertzenberg |
| 4,667,846 A | 5/1987 | Marceau |
| 4,747,365 A | 5/1988 | Tusch |
| 4,756,299 A | 7/1988 | Podella |
| 4,798,691 A | 1/1989 | Kasai et al. |
| 4,853,266 A | 8/1989 | Cullen |
| 4,872,442 A | 10/1989 | Manker |
| 4,880,953 A | 11/1989 | Manker |
| 4,904,524 A | 2/1990 | Yoh |
| 4,923,645 A | 5/1990 | Tsang et al. |
| 4,964,543 A | 10/1990 | Scheiber |
| 4,978,560 A | 12/1990 | Stone |
| 4,984,530 A | 1/1991 | Dutton |
| 4,991,538 A | 2/1991 | Davids et al. |
| 5,035,321 A | 7/1991 | Denton |
| 5,045,569 A | 9/1991 | Delgado |
| 5,071,706 A | 12/1991 | Soper |
| 5,107,734 A | 4/1992 | Armbruster |
| 5,156,885 A | 10/1992 | Budd |
| 5,180,637 A | 1/1993 | Sumii |
| 5,184,613 A | 2/1993 | Mintz |
| 5,187,011 A | 2/1993 | Manalastas |
| 5,192,615 A | 3/1993 | McDougall |
| 5,194,356 A | 3/1993 | Sacripante et al. |
| 5,204,183 A | 4/1993 | McDougall |
| 5,232,769 A | 8/1993 | Yamato et al. |
| 5,265,509 A | 11/1993 | Chen |
| 5,284,703 A | 2/1994 | Everhart et al. |
| 5,339,796 A | 8/1994 | Manker |
| 5,350,624 A | 9/1994 | Georger et al. |
| 5,366,801 A | 11/1994 | Bryant et al. |
| 5,375,616 A | 12/1994 | Chen |
| 5,385,737 A | 1/1995 | Shigeno et al. |
| 5,392,945 A | 2/1995 | Syrek |
| 5,401,601 A | 3/1995 | Sacripante et al. |
| 5,415,222 A | 5/1995 | Colvin et al. |
| 5,425,975 A | 6/1995 | Koiso et al. |
| 5,435,465 A | 7/1995 | El-Amin |
| 5,439,104 A | 8/1995 | Wolska-Klis |
| 5,443,084 A | 8/1995 | Saleur |
| 5,462,197 A | 10/1995 | Pound |
| 5,484,895 A | 1/1996 | Meister et al. |
| 5,507,389 A | 4/1996 | Syrek |
| 5,538,531 A | 7/1996 | Hudson et al. |
| 5,589,194 A | 12/1996 | Tsuei et al. |
| 5,598,954 A | 2/1997 | Salzonao |
| 5,618,008 A | 4/1997 | Dearwester et al. |
| 5,624,025 A | 4/1997 | Hixon |
| 5,637,389 A | 6/1997 | Colvin et al. |
| 5,656,708 A | 8/1997 | Meister |
| 5,660,636 A | 8/1997 | Shangold et al. |
| 5,677,048 A | 10/1997 | Pushaw |
| 5,697,577 A | 12/1997 | Ogden |
| 5,712,212 A | 1/1998 | Scott et al. |
| 5,725,888 A | 3/1998 | Scott et al. |
| 5,728,454 A | 3/1998 | Inaba et al. |
| 5,733,272 A | 3/1998 | Brunner et al. |
| 5,738,082 A | 4/1998 | Page et al. |
| 5,747,004 A | 5/1998 | Giani et al. |
| 5,762,710 A | 6/1998 | Ngai et al. |
| 5,780,047 A | 7/1998 | Kamiya et al. |
| 5,785,179 A | 7/1998 | Buczwinski et al. |
| 5,819,989 A | 10/1998 | Saraceni |
| 5,839,608 A | 11/1998 | Gillberg-LaForce |
| 5,887,759 A | 3/1999 | Ayigbe |
| 5,944,709 A | 8/1999 | Barney et al. |
| 5,951,762 A | 9/1999 | Shangold et al. |
| 5,975,074 A | 11/1999 | Koiso et al. |
| 6,021,920 A | 2/2000 | Aldape |
| 6,057,372 A | 5/2000 | Nobuhiro |
| 6,059,882 A | 5/2000 | Steinhardt et al. |
| 6,063,406 A | 5/2000 | Hornack |
| 6,085,899 A | 7/2000 | Thorsbakken |
| 6,099,555 A | 8/2000 | Sabin |
| 6,121,165 A | 9/2000 | Mackey et al. |
| 6,127,294 A | 10/2000 | Koiso et al. |
| 6,170,426 B1 | 1/2001 | Thorsbakken |
| 6,171,647 B1 | 1/2001 | Holman |
| 6,180,124 B1 | 1/2001 | Ohta et al. |
| 6,207,738 B1 | 3/2001 | Zuckerman et al. |
| 6,213,424 B1 | 4/2001 | Helfer-Grand |
| 6,216,920 B1 | 4/2001 | Baggett |
| 6,217,889 B1 | 4/2001 | Lorenzi et al. |
| 6,238,682 B1 | 5/2001 | Klofta et al. |
| 6,267,975 B1 | 7/2001 | Smith, III et al. |
| 6,269,969 B1 | 8/2001 | Huang et al. |
| 6,287,580 B1 | 9/2001 | Gott et al. |
| 6,314,971 B1 | 11/2001 | Schneider |
| 6,319,318 B1 | 11/2001 | Pekarek et al. |
| 6,321,937 B1 | 11/2001 | Desimone et al. |
| 6,322,801 B1 | 11/2001 | Lorenzi et al. |
| 6,343,491 B1 | 2/2002 | Jung |
| 6,346,153 B1 | 2/2002 | Lake et al. |
| 6,355,281 B1 | 3/2002 | Cerchiari et al. |
| 6,387,385 B1 | 5/2002 | Wang |
| 6,401,968 B1 | 6/2002 | Huang et al. |
| 6,431,111 B1 | 8/2002 | Zhang |
| 6,436,128 B1 | 8/2002 | Usui |
| 6,457,434 B1 | 10/2002 | Lazar |
| 6,484,514 B1 | 11/2002 | Joseph et al. |
| 6,503,976 B2 | 1/2003 | Zuckerman et al. |
| 6,514,362 B1 | 2/2003 | Zuckerman et al. |
| 6,520,942 B1 | 2/2003 | Putman |
| 6,528,766 B1 | 3/2003 | Parks et al. |
| 6,547,063 B1 | 4/2003 | Zaveri et al. |
| 6,547,881 B1 | 4/2003 | Klackner |
| 6,550,633 B2 | 4/2003 | Huang et al. |
| 6,562,318 B1 | 5/2003 | Filler |
| 6,579,570 B1 | 6/2003 | Lang et al. |
| 6,592,004 B2 | 7/2003 | Huang et al. |
| 6,601,737 B1 | 8/2003 | Sandler |
| 6,613,144 B1 | 9/2003 | Loertscher et al. |
| 6,663,686 B1 | 12/2003 | Geiger et al. |
| 6,673,358 B1 | 1/2004 | Cole et al. |
| 6,680,084 B1 | 1/2004 | Chtourou |
| 6,708,845 B2 | 3/2004 | Weng |
| 6,726,386 B1 | 4/2004 | Gruenbacher et al. |
| 6,742,689 B2 | 6/2004 | Formon et al. |
| 6,749,148 B2 | 6/2004 | Helfer-Grand |
| 6,752,998 B2 | 6/2004 | Verdrel-Lahaxe et al. |
| 6,766,919 B2 | 7/2004 | Huang et al. |
| 6,831,051 B2 | 12/2004 | Sommerville-Roberts et al. |

| | | | | | | |
|---|---|---|---|---|---|---|
| 6,838,154 | B1 | 1/2005 | Varona et al. | DE | 1026453 A1 | 11/2001 |
| 6,847,011 | B2 | 1/2005 | McConnell et al. | DE | 10205872 A2 | 3/2003 |
| 6,858,666 | B2 | 2/2005 | Hamer et al. | DE | 10209111 A1 | 9/2003 |
| 6,863,682 | B2 | 3/2005 | Usui | DE | 20305272 | 9/2003 |
| 6,890,553 | B1 | 5/2005 | Sun et al. | DE | 10234257 | 2/2004 |
| 6,890,592 | B2 | 5/2005 | Seehafer et al. | DE | 10361100 A1 | 1/2005 |
| 6,903,307 | B1 | 6/2005 | McConnell et al. | DE | 102005002169 A1 | 7/2006 |
| 6,918,513 | B1 | 7/2005 | Downey | DE | 1005042236 A | 3/2007 |
| 6,946,413 | B2 | 9/2005 | Lange et al. | EP | 0247864 | 12/1987 |
| 6,952,849 | B2 | 10/2005 | Pacella | EP | 0252553 B1 | 1/1988 |
| 6,958,103 | B2 | 10/2005 | Anderson et al. | EP | 0288909 A1 | 11/1988 |
| 7,021,848 | B1 | 4/2006 | Gruenbacher et al. | EP | 0351907 A2 | 1/1990 |
| 7,101,612 | B2 | 9/2006 | Lang et al. | EP | 0365160 A2 | 4/1990 |
| 7,108,440 | B1 | 9/2006 | Gruenbacher et al. | EP | 0370600 A1 | 5/1990 |
| 7,211,249 | B2 | 5/2007 | Schnittger et al. | EP | 0436729 | 7/1991 |
| 7,229,611 | B2 | 6/2007 | Zamudio-Tena et al. | EP | 0897719 A1 | 2/1999 |
| 7,238,655 | B2 | 7/2007 | Ness | EP | 0953312 A1 | 11/1999 |
| 2002/0044968 | A1 | 4/2002 | van Lengerich | EP | 0974340 A2 | 1/2000 |
| 2002/0050659 | A1 | 5/2002 | Toreki et al. | EP | 1038793 A1 | 9/2000 |
| 2002/0061954 | A1 | 5/2002 | Davis et al. | EP | 1084670 A2 | 3/2001 |
| 2002/0086045 | A1 | 7/2002 | Wang | EP | 1166866 A | 1/2002 |
| 2002/0102488 | A1 | 8/2002 | Yanaka et al. | EP | 1181911 A1 | 2/2002 |
| 2002/0155281 | A1 | 10/2002 | Lang et al. | EP | 1186286 A1 | 3/2002 |
| 2002/0174863 | A1 | 11/2002 | Saric et al. | EP | 1191092 A | 3/2002 |
| 2002/0192268 | A1 | 12/2002 | Alwattari et al. | EP | 1229097 A1 | 8/2002 |
| 2003/0082217 | A1 | 5/2003 | Afriat et al. | EP | 1247568 A1 | 10/2002 |
| 2003/0084914 | A1 | 5/2003 | Simon | EP | 1310186 | 5/2003 |
| 2003/0105192 | A1 | 6/2003 | Li et al. | EP | 1334921 A2 | 8/2003 |
| 2003/0118779 | A1 | 6/2003 | Fish et al. | EP | 0994650 B1 | 2/2004 |
| 2003/0175517 | A1 | 9/2003 | Voigt et al. | EP | 1402879 | 3/2004 |
| 2003/0198652 | A1 | 10/2003 | Shefer et al. | EP | 1407762 | 4/2004 |
| 2003/0228351 | A1 | 12/2003 | Hassenoehrl et al. | EP | 1410753 A1 | 4/2004 |
| 2003/0232090 | A1 | 12/2003 | Ahmad et al. | EP | 1421872 A2 | 5/2004 |
| 2004/0062732 | A1 | 4/2004 | Friscia et al. | EP | 1051478 B1 | 11/2004 |
| 2004/0062735 | A1 | 4/2004 | Sun et al. | EP | 1479432 A1 | 11/2004 |
| 2004/0063603 | A1 | 4/2004 | Dave et al. | EP | 1495704 A | 1/2005 |
| 2004/0069298 | A1 | 4/2004 | Minami | EP | 1586308 A1 | 10/2005 |
| 2004/0084791 | A1 | 5/2004 | Han et al. | FR | 2669205 A1 | 5/1992 |
| 2004/0116017 | A1 | 6/2004 | Smith, III et al. | FR | 2823137 A1 | 10/2002 |
| 2004/0118862 | A1 | 6/2004 | Amundson | GB | 1291377 | 10/1972 |
| 2004/0121072 | A1 | 6/2004 | Xing et al. | GB | 1370633 A | 10/1974 |
| 2004/0147189 | A1 | 7/2004 | Smith, III et al. | GB | 2142135 A | 1/1985 |
| 2004/0164085 | A1 | 8/2004 | Kitching et al. | GB | 2168031 A | 6/1986 |
| 2004/0169299 | A1 | 9/2004 | Davis et al. | GB | 2192171 A | 1/1988 |
| 2004/0185023 | A1 | 9/2004 | Schnittger et al. | GB | 2297490 A | 8/1996 |
| 2004/0265589 | A1 | 12/2004 | Yamada et al. | GB | 2394898 | 5/2004 |
| 2005/0048090 | A1 | 3/2005 | Rau | JP | 63168484 A | 6/1988 |
| 2005/0053647 | A1 | 3/2005 | Matusch et al. | JP | 02142561 A | 5/1990 |
| 2005/0067423 | A1 | 3/2005 | Cho | JP | 03152894 A | 6/1991 |
| 2005/0067726 | A1 | 3/2005 | Yan et al. | JP | 08067869 | 3/1996 |
| 2005/0113771 | A1 | 5/2005 | MacDonald et al. | JP | 08067869 A | 3/1996 |
| 2005/0136765 | A1 | 6/2005 | Shannon | JP | 08112303 A | 5/1996 |
| 2005/0158395 | A1 | 7/2005 | Zimmermann et al. | JP | 08173471 A | 7/1996 |
| 2005/0169868 | A1 | 8/2005 | Mohammadi et al. | JP | 09047376 | 2/1997 |
| 2005/0214242 | A1 | 9/2005 | Mohammadi et al. | JP | 10077134 | 3/1998 |
| 2005/0226834 | A1 | 10/2005 | Lambino et al. | JP | 10077134 A | 3/1998 |
| 2005/0250169 | A1 | 11/2005 | Gonzalez et al. | JP | 2002020739 A | 1/2002 |
| 2006/0018953 | A1 | 1/2006 | Guillon et al. | JP | 2003104465 | 4/2003 |
| 2006/0159776 | A1 | 7/2006 | Ward | WO | 9219141 | 11/1992 |
| 2006/0173576 | A1 | 8/2006 | Goerg et al. | WO | 9304622 | 3/1993 |
| 2006/0270585 | A1 | 11/2006 | Jordan, IV et al. | WO | 9322961 A1 | 11/1993 |
| 2006/0270586 | A1 | 11/2006 | Jordan, IV et al. | WO | 9924159 A1 | 5/1999 |
| 2006/0276356 | A1 | 12/2006 | Panandiker et al. | WO | 9937747 A1 | 7/1999 |
| 2007/0027415 | A1 | 2/2007 | Kopreski | WO | 0043286 A1 | 7/2000 |
| | | | | WO | 0103619 A1 | 1/2001 |
| | | FOREIGN PATENT DOCUMENTS | | WO | 0106903 | 2/2001 |
| DE | | 2912972 C2 | 8/1982 | WO | 0108658 A1 | 2/2001 |
| DE | | 3101471 A1 | 8/1982 | WO | 0112147 A1 | 2/2001 |
| DE | | 3447833 A1 | 7/1986 | WO | 0112148 A1 | 2/2001 |
| DE | | 3535330 A1 | 4/1987 | WO | 0112149 A1 | 2/2001 |
| DE | | 3922159 A1 | 1/1991 | WO | 0126994 A1 | 4/2001 |
| DE | | 29809967 U1 | 10/1998 | WO | 0135906 A1 | 5/2001 |
| DE | | 19716254 A1 | 1/1999 | WO | 0139704 A1 | 6/2001 |
| DE | | 19846375 A1 | 4/2000 | WO | 0139705 A1 | 6/2001 |
| DE | | 19920685 A1 | 11/2000 | WO | 0142117 | 6/2001 |
| DE | | 19937884 A1 | 2/2001 | WO | 0154661 A1 | 8/2001 |
| DE | | 10002590 A1 | 8/2001 | WO | 0160298 A2 | 8/2001 |
| DE | | 10009252 | 9/2001 | WO | 0160305 A1 | 8/2001 |
| DE | | 20108351 U1 | 10/2001 | WO | 0164525 | 9/2001 |

| | | |
|---|---|---|
| WO | 0176439 | 10/2001 |
| WO | 0189353 | 11/2001 |
| WO | 0201129 A1 | 1/2002 |
| WO | 0206421 A1 | 1/2002 |
| WO | 0226911 A | 4/2002 |
| WO | 03000089 | 1/2003 |
| WO | 03000487 A2 | 1/2003 |
| WO | 03005876 A1 | 1/2003 |
| WO | 03018186 A1 | 3/2003 |
| WO | 03028515 | 4/2003 |
| WO | 03048654 A | 6/2003 |
| WO | 03049939 A1 | 6/2003 |
| WO | 03099427 A1 | 12/2003 |
| WO | 2004014540 A1 | 2/2004 |
| WO | 2004016234 A1 | 2/2004 |
| WO | 2004033340 A1 | 4/2004 |
| WO | 2004041134 A1 | 5/2004 |
| WO | 2004041251 A1 | 5/2004 |
| WO | 2004047977 A1 | 6/2004 |
| WO | 2004066800 | 8/2004 |
| WO | 2004105709 A1 | 12/2004 |
| WO | 2004108075 A2 | 12/2004 |
| WO | 2005011855 A1 | 2/2005 |
| WO | 2005011856 A1 | 2/2005 |
| WO | 2005018795 A1 | 3/2005 |
| WO | WO 2005018794 A1 * | 3/2005 |
| WO | 2005055790 | 6/2005 |
| WO | 2005087068 | 9/2005 |
| WO | 2005093029 | 10/2005 |
| WO | 2007075207 A | 7/2007 |
| WO | 2007075208 A | 7/2007 |
| WO | 2007075209 A | 7/2007 |
| WO | 2007075211 A | 7/2007 |
| WO | 2007075216 A | 7/2007 |
| WO | 2007078362 A | 7/2007 |
| WO | 2007078373 | 7/2007 |
| WO | 2007078393 | 7/2007 |
| WO | 2007078400 | 7/2007 |

OTHER PUBLICATIONS

Office Action regarding U.S. Appl. No. 11/319,953, dated Dec. 12, 2008.
Office Action regarding U.S. Appl. No. 11/610,970, dated Dec. 26, 2008.
Nonfinal Office Action dated Jan. 10, 2008 regarding U.S. Appl. No. 11/747,036, 7 pages.
Final Office Action dated Jan. 25, 2008 regarding U.S. Appl. No. 11/320,369, 16 pages.
Office Action dated Mar. 18, 2008 regarding U.S. Appl. No. 11/420,993, 7 pages.
International Search Report and Written Opinion regarding PCT/IB2007/054644, dated May 21, 2008.
International Search Report and Written Opinion regarding PCT/IB2007/054645, dated May 20, 2008.
International Search Report and Written Opinion regarding PCT/IB2007/054642, dated Jun. 3, 2008.
Office action from U.S. Appl. No. 11/319,953, dated May 1, 2008.
Non-final Office Action for U.S. Appl. No. 11/320,369 dated Jul. 3, 2007.
Non-final Office Action for U.S. Appl. No. 11/319,856 dated Jul. 2, 2007.
International Search Report and Written Opinion regarding PCT/IB2007/054643, dated Jul. 2, 2008.
Non-final Office Action, Jul. 8, 2008 (U.S. Appl. No. 11/320,369) 13 pages.
Non-final Office Action, U.S. Appl. No. 11/420,988 (Aug. 22, 2008).
Non-final Office Action regarding U.S. Appl. No. 11/319,881, dated Aug. 20, 2008.
Non-Final Office Action regarding U.S. Appl. No. 11/420,980, dated Sep. 25, 2008.
Office Action dated Oct. 1, 2007 regarding U.S. Appl. No. 11/319,881, 9 pages.
Office Action dated Oct. 1, 2007 regarding U.S. Appl. No. 11/320,363, 7 pages.
Griffin, "Classification of Surface-Active Agents by "HLB,"" Journal of the Society of Cosmetic Chemists, vol. 1, pp. 311-326, 1949.
Rosen, Delivery System Handbook for Personal Care and Cosmetic Products—Technology, Applications and Formulations, 2005, William Andrew Publishing, pp. 259-263, online version available at http://www.knovel.com/knovel2/Toc.jsp?BookID=1280&VerticalID=0.
Nonfinal Office action from U.S. Appl. No. 11/319,953, dated Nov. 19, 2007.
International Search Report and Written Opinion regarding PCT/IB2007/051691, 24 pages (Nov. 27, 2007).
International Search Report and Written Opinion from PCT/IB2007/051671, dated Nov. 27, 2007.
Non-final Office Action, U.S. Appl. No. 11/609,701 (Apr. 2, 2009).
Non-final Office Action, U.S. Appl. No. 11/319,853 (Apr. 1, 2009).
Non-final Office Action, U.S. Appl. No. 11/320,247 (Apr. 3, 2009).
Non-final Office Action from U.S. Appl. No. 11/610,985, dated Jun. 8, 2009.
Non-final Office Action, U.S. Appl. No. 11/420,980 (Mar. 12, 2009).
Non-final Office Action from U.S. Appl. No. 11/320,049, dated May 4, 2009.
Office Action dated Mar. 25, 2008 regarding U.S. Appl. No. 11/320,363.
Office Action dated Mar. 20, 2008 regarding U.S. Appl. No. 11/319,881.
Final Office Action regarding U.S. Appl. No. 11/610,966, dated Aug. 7, 2009.
Final Office Action regarding U.S. Appl. No. 11/319,881, dated Jul. 13, 2009.
Non-final Office Action regarding U.S. Appl. No. 11/319,881, dated Feb. 6, 2009.
Non-final Office Action regarding U.S. Appl. No. 12/174,459, dated Feb. 5, 2009.
Non-final Office Action, U.S. Appl. No. 11/420,988 (Feb. 25, 2009).
Non-final Office Action, U.S. Appl. No. 11/320,363 (Mar. 3, 2009).
Non-final Office Action regarding U.S. Appl. No. 11/320,369 (Jan. 27, 2009).
Final Office Action regarding U.S. Appl. No. 11/319,953, dated Apr. 28, 2009.
Final Office Action regarding U.S. Appl. No. 11/320,363, dated Aug. 14, 2009.
Final Office Action regarding U.S. Appl. No. 12/174,459, dated Aug. 5, 2009.
Notice of Allowance regarding U.S. Appl. No. 11/420,988, dated Sep. 21, 2009.
Non-final Office action regarding U.S. Appl. No. 11/319,953, dated Sep. 2, 2009.
Non-final Office action regarding U.S. Appl. No. 11/320,363, dated Dec. 31, 2009.
Non-final Office action regarding U.S. Appl. No. 11/610,985, dated Dec. 9, 2009.
Non-final Office Action issued in U.S. Appl. No. 11/610,985, dated Dec. 9, 2009.
Australian Examiners Report for Patent Application No. 2006330094 dated Jul. 21, 2011; 3 pages.
Australian First Report for Patent Application No. 2006333485 dated Jul. 21, 2011; 3 pages.
European Official Communication for EP 07849139.6 mailed Dec. 22, 2010.
International Search Report and Written Opinion from PCT/US2006/042050, dated May 2, 2007.
Final Office action issued in U.S. Appl. No. 11/320,363, dated Jun. 10, 2010.
Non-final Office action issued in U.S. Appl. No. 11/610,985 issued on Apr. 27, 2011.
Final Office Action issued in related U.S. Appl. No. 11/610,985, dated Jun. 15, 2010.
Final Office action issued in U.S. Appl. No. 11/610,985 (dated Aug. 31, 2010).
International Search Report for PCT/US2006/039138 dated Feb. 16, 2007.
International Search Report for PCT/US2006/041939 dated Mar. 8, 2007.

International Search Report for PCT/US2006/038271 dated May 3, 2007.

Ahlstrom, B., et al., "The Effect of Hydrocarbon Chain Length, pH, and Temperature on the Binding and Bactericidal Effect of Amphiphilic Betaine Esters on *Salmonella* typhimurium," APMIS, Mar. 1999, pp. 318-324 , 107 (3).

Ahlstrom, B., et al., "Loss of Bactericidal Capacity of Long-chain Quaternary Ammonium Compounds with Protein at Lowered Temperature," APMIS, Jun. 1999, pp. 606-614, 107(6).

Akiyama, H., et al., "Antimicrobial Effects of Acidic Hot-Spring Water on *Staphlycococcus aureus* Strains Isolated from Atopic Dermatitis Patients," J. Dermatol. Sci., Nov. 2000, pp. 112-118, 24(2).

Bengoechea, J., et al., "Temperature-Regulated Efflux Pump/Potassium Antiporter System Mediates Resistance to Cationic Antimicrobial Peptides in *Yersinia*," Mol. Microbiol. Jul. 2000, pp. 67-80, 37(1).

CRC Handbook of Chemistry and Physics, 72nd Ed., 1991-92, pp. 5-83-5-90.

Del Campo, J., et al., "Antimicrobial Effect of Rosemary Extracts," J. Food Prot., Oct. 2000, pp. 1359-1368, 63 (10).

Folwaczny, M., et al., "Antibacterial Effects of Pulsed Nd:YAG Laser Radiation at Different Energy Settings in Root Canals," J. Endod., Jan. 2002, pp. 24-29, 28(1).

Martinez, M., et al., "Reduced Outer Membrane Permeability of *Escherichia coli* O157:H7: Suggested Role of Modified Outer Membrane Porins and Theoretical Function in Resistance to Antimicrobial Agents," Biochemistry, Oct. 9, 2001, pp. 11965-11974, 40(40).

Moro, M., et al., "Effects of Heat Stress on the Antimicrobial Drug Resistance of *Escherichia coli* of the Instestinal Flora of Swine," J. Appl. Microbiol., May 2000, pp. 836-844, 88(5).

Niwa, M., et al., "Differential Uptake of Grepafloxacin by Human Circulating Blood Neutrophils and Those Exudated into Tissues," Eur. J. Pharmacol., Sep. 28, 2001, pp. 121-126, 428(1).

Lange, N., Lange's Handbook of Chemistry, 11th Ed., 1973, pp. 9-107-9-115, McGraw-Hill Book Company, New York, U.S.

Raj, P., et al., "Synthesis, Microbicidal Activity, and Solution Structure of the Dodecapeptide from Bovine Neutrophils," Biopolymers, Apr. 5, 2000, pp. 281-292, 53(4).

Technical Textiles International, "Phase Change Materials Shown Potential for Medical Applications," Sep. 1999.

Yamaguchi, S., et al., "Orientation and Dynamics of an Antimicrobial Peptide in the Lipid Bilayer by Solid-State NMR Spectroscopy," Biophys. J., Oct. 2001, pp. 2203-2214, 81(4).

International Cosmetic Ingredient Dictionary and Handbook, 10th Ed., vol. 3, pp. 2294-2296 (2004).

Araki et al., "Measurements of Thermophysical Properties of Sodium Acetate Hydrate," International J. of Thermo., 16(6): 1455-1466 (1995).

K. Sturley, "Fresh Data on the Latent Heats and Heat conductivities of Some Aqua-Crystalline Compounds," J. of the Society of Chem. Industr., 51:271T-273T (Aug. 12, 1932).

Chatterji et al., "The Rate of Crystal Growth in Supersaturated Solutions, Part I," J. Indian Chem. Soc., 28(12): 599-601 (Dec. 1951).

M. Telkes, "Nucleation of Supersaturated Inorganic Salt Solutions," Industrial and Engineering Chemistry, 44/6: 1308-1310 (Jun. 1952).

Dietz, Jr. et al., "Linear Crystallization Velocities of Sodium Acetate in Supersaturated Solutions," J. Phys. Chem., 61(7): 944-948 (Jul. 1957).

Meisingset, et al., "Thermodynamic Properties and Phase Transitions of Salt Hydrates between 270 and 400 K," J. Chem. Thermodynamics, 16(1-6): 523-536 (Jan. 1984).

Wada, et al., "Heat Storage Capacity of Sodium Acetate Trihydrate during Thermal Cycling," Solar Energy, 33(3/4): 373-375 (1984).

J.C. Deelman, Mechanism of formation of Magnesite and Dolomite, Ch. 8, pp. 278-329 (2003).

Rogerson, et al., "Solidification of Heat Packs: 1. Nucleation Rate," AIChE Journal, 49(2): 505-529 (Feb. 2003).

A.V. Patel, et al., "A Novel Encapsulation Technique for the Production of Artificial Seeds," Plant Cell Reports, 19: 868-874 (2000).

International Search Report for PCT/US2006/039137 dated Mar. 23, 2007.

International Search Report for PCT/US2006/042435 dated Mar. 23, 2007.

International Search Report for PCT/US2006/038914 dated Mar. 23, 2007.

International Search Report and Written Opinion from PCT/US2006/038834, dated Apr. 11, 2007.

International Search Report and Written Opinion from PCT/US2006/038915, dated Apr. 5, 2007.

Non-final Office action regarding U.S. Appl. No. 12/267,007, dated May 10, 2010.

* cited by examiner

MICROENCAPSULATED DELIVERY VEHICLE HAVING AN AQUEOUS CORE

BACKGROUND OF THE DISCLOSURE

The present disclosure relates generally to microencapsulated delivery vehicles including an active agent and processes for producing the same, as well as products incorporating the microencapsulated delivery vehicles and processes for producing the products. More particularly, the present disclosure is directed to microencapsulated delivery vehicles that can provide a functional benefit such as a skin care benefit and can be effectively utilized in a wipe or similar product such that, upon use and activation, the contents of the microencapsulated delivery vehicles are released and a benefit is provided. The microencapsulated delivery vehicles may include one or more moisture protective and fugitive layers to improve overall capsule performance.

Many consumer products on today's market include active agents to improve the product's characteristics and function. The active agents can be any material that acts upon a substrate or otherwise provides a benefit once activated. Examples of active agents that may enhance the value of a product include skin care benefit agents that are intended to be transferred to the external skin by personal care products such as wipes, lotions, emulsions, balms, and the like to provide for cleansing and conditioning. Additional active agents include pharmaceuticals that are intended to be ingested, transferred transdermally, or subcutaneously injected into a human or animal patient's body, vitamins and nutrients, and various other agents that can be similarly introduced into or onto the body of a patient.

Additionally, non-pharmaceutical active agents can be incorporated into consumer products to improve the product's overall value. For example, products whose use is mainly for outdoors, such as deck furniture and automobile covers, could benefit by having UV absorbing active agents (UV absorbers) incorporated onto their surfaces. By absorbing UV rays, these agents could provide an outdoor product having improved aesthetic properties and durability.

While the desire to incorporate these types of active agents is known, the present methods for providing products with these agents can be expensive and complex. Specifically, the present methods require the use of complex chemical formulations and long, complex chemical processes to incorporate the agents into or onto a product. Furthermore, many times the active agents will degrade over time due to the conditions of manufacturing, storage, and transportation of the product. As such, at the time of intended use, the active agents are no longer present to provide the desired benefits.

Based on the foregoing, there is a need in the art for delivery vehicles that can inexpensively and efficiently deliver active agents to various consumer products. Additionally, it would be advantageous if the delivery vehicles could prevent the active agents from being released prematurely so as to provide a benefit at the desired point of use of the product.

SUMMARY OF THE DISCLOSURE

The present disclosure relates to microencapsulated delivery vehicles suitable for use in various products, such as personal care products including wet wipes, dry wipes, lotions, creams, cloths, and the like.

In one embodiment, the microencapsulated delivery vehicles, upon activation in a wet wipe, for example, can produce a skin benefit when the wet wipe is used. The microencapsulated delivery vehicles include an aqueous core composition comprising an encapsulating activator, a matrix material, such as water, and an active agent, such as a skin conditioner. Optionally, the aqueous core composition may also include a surfactant and a hydrophobic wax material surrounding the active agent to improve overall performance. In some cases, the aqueous core composition of the microencapsulated delivery vehicle may contain a small amount of un-used encapsulating activator as described herein. The aqueous core composition and components therein are encapsulated in a thin capsule that may have one or more moisture protective layers and/or fugitive layers thereon to impart additional advantageous characteristics. Upon use in a wet wipe, the capsules containing the aqueous core composition including the matrix material and active agent (and any other optional components) are ruptured such that the active agent present in the wet wipe solution is released to provide a benefit to a substrate, such as skin.

In another embodiment, the active agent is a heating agent. By using a heating agent, the microencapsulated delivery vehicles, upon activation in a wet wipe, for example, can produce a warming sensation on the skin when the wet wipe is used.

The present disclosure also relates to processes for manufacturing a microencapsulated delivery vehicle suitable for use in personal care products, such as wet wipes. In one embodiment, a composition including an aqueous core composition comprising an encapsulating activator, a matrix material, such as water, and an active agent that may or may not be surrounded by a hydrophobic wax material, and optionally, a surfactant, is introduced into a liquid solution containing a crosslinkable compound. Once in the liquid solution, the encapsulating activator reacts with the crosslinkable compound to form an encapsulation layer that surrounds the aqueous core composition. After a sufficient time has passed, the encapsulated aqueous core composition containing the active agent is removed from the liquid solution. Optionally, the encapsulated aqueous core composition may then be subjected to one or more further processing steps to introduce additional layers of encapsulation onto the formed shell. These layers may include, for example, a moisture protective layer to reduce the potential for deactivation of the active agent due to leaking of the agent from the capsule into the product, and a fugitive layer to impart mechanical strength to the capsule.

As such, the present disclosure is directed to a microencapsulated delivery vehicle comprising an aqueous core composition surrounded by an encapsulation layer. The aqueous core composition comprises an encapsulating activator, a matrix material, and an active agent. The microencapsulated delivery vehicle has a diameter of from about 5 micrometers to about 5000 micrometers.

The present disclosure is further directed to a substantially fluid-impervious microencapsulated delivery vehicle comprising an aqueous core composition, an encapsulation layer surrounding the aqueous core composition, and a moisture protective layer surrounding the encapsulation layer. The aqueous core composition comprises an encapsulating activator, a matrix material, and an active agent and the microencapsulated delivery vehicle has a diameter of from about 5 micrometers to about 5000 micrometers.

The present disclosure is further directed to a stabilized microencapsulated delivery vehicle comprising an aqueous core composition, an encapsulation layer surrounding the aqueous core composition, and a fugitive layer surrounding the encapsulation layer. The aqueous core composition comprises an encapsulating activator, a matrix material, and an active agent, and the microencapsulated delivery vehicle has a diameter of from about 5 micrometers to about 5000 micrometers.

The present disclosure is further directed to a microencapsulated delivery vehicle comprising an aqueous core composition surrounded by an encapsulation layer. The aqueous core composition comprises an encapsulating activator, a matrix material, and a heating agent. The microencapsulated delivery vehicle has a diameter of from about 5 micrometers to about 5000 micrometers.

Other features of the present disclosure will be in part apparent and in part pointed out hereinafter.

DEFINITIONS

Figure 1:
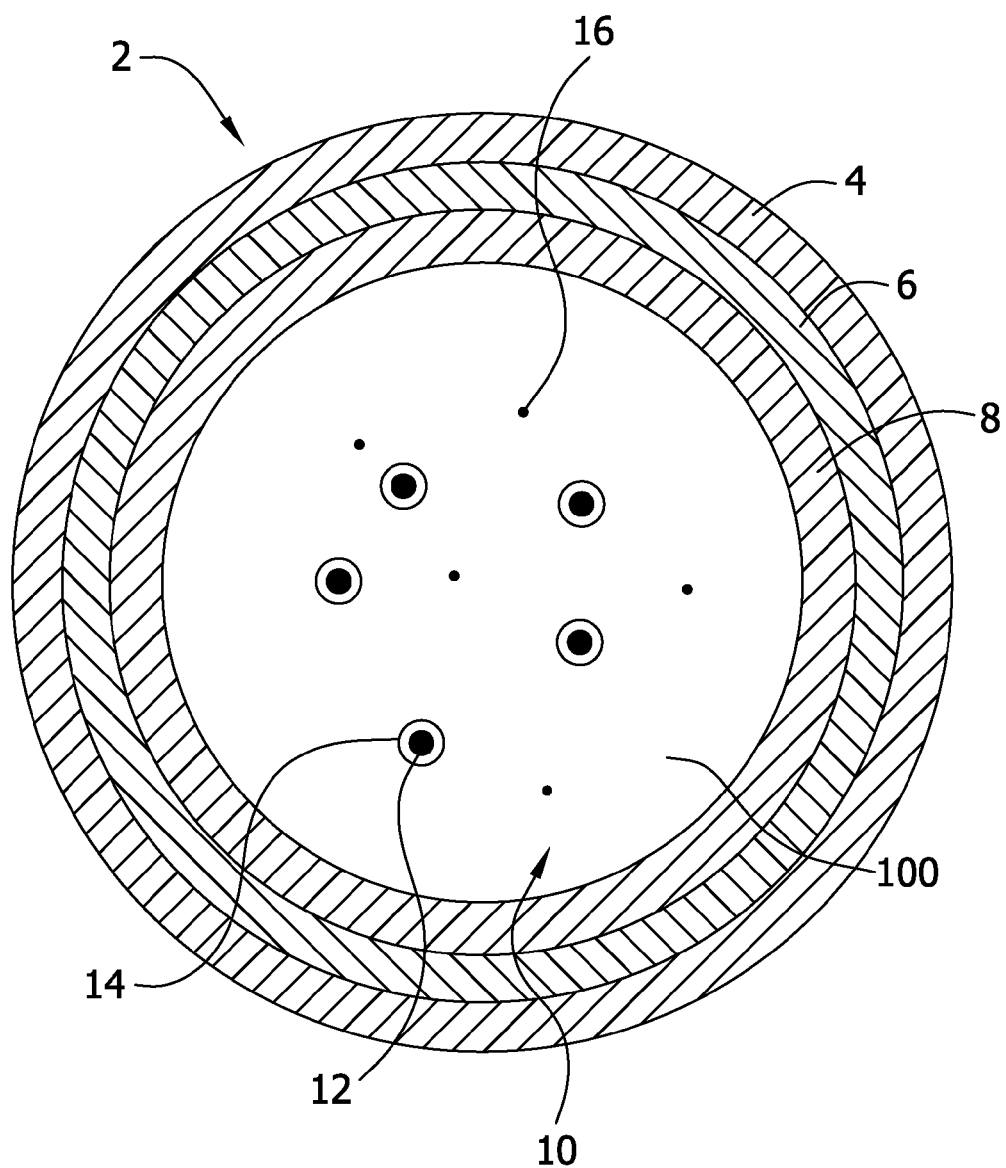
FIG. 1 depicts a cross sectional view of a microencapsulated delivery vehicle of the present disclosure.

Within the context of this specification, each term or phrase below will include, but not be limited to, the following meaning or meanings:
  (a) "Bonded" refers to the joining, adhering, connecting, attaching, or the like, of two components. Two components will be considered to be bonded together when they are bonded directly to one another or indirectly to one another, such as when each is directly bonded to intermediate elements.
  (b) "Film" refers to a thermoplastic film made using a film extrusion and/or forming process, such as a cast film or blown film extrusion process. The term includes apertured films, slit films, and other porous films which constitute liquid transfer films, as well as films which do not transfer liquid.
  (c) "Layer" when used in the singular can have the dual meaning of a single element or a plurality of elements.
  (d) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. (Nov. 19, 1974). Meltblown fibers are microfibers which may be continuous or discontinuous, are generally smaller than about 0.6 denier, and are generally self bonding when deposited onto a collecting surface. Meltblown fibers used in the present disclosure are preferably substantially continuous in length.
  (e) "Nonwoven" refers to materials and webs of material which are formed without the aid of a textile weaving or knitting process.
  (f) "Polymeric" includes, but is not limited to, homopolymers, copolymers, such as for example, block, graft, random and alternating copolymers, terpolymers, etc. and blends and modifications thereof. Furthermore, unless otherwise specifically limited, the term "polymeric" shall include all possible geometrical configurations of the material. These configurations include, but are not limited to, isotactic, syndiotactic and atactic symmetries.
  (g) "Thermoplastic" describes a material that softens when exposed to heat and which substantially returns to a nonsoftened condition when cooled to room temperature.

DETAILED DESCRIPTION OF THE PREFERRED EMBODIMENT

The present disclosure relates to microencapsulated delivery vehicles suitable for use in products such as personal care products including, for example, wet wipes and dry wipes. In one embodiment, the microencapsulated delivery vehicles, upon activation, are capable of providing a skin care benefit on the skin of a user of the wet wipe. In another embodiment, the microencapsulated delivery vehicles, upon activation, are capable of providing a warming sensation on the skin of a user of the wet wipe. The microencapsulated delivery vehicles as described herein may include one or more encapsulating layers, moisture protective layers, and fugitive layers to impart various characteristics upon the encapsulated vehicles and the products in which they are used. Surprisingly, it has been discovered that an encapsulating activator can be included directly within an aqueous core composition and the combination introduced into a solution containing a crosslinkable compound and the thickness of the resulting crosslinked encapsulation layer can be closely controlled.

Although discussed primarily herein in relation to microencapsulated delivery vehicles providing for a skin care benefit, it will be recognized by one skilled in the art based on the disclosure herein that other active agents or active ingredients, in addition to, or in place of, the skin care benefit agent, may be incorporated into the microencapsulated delivery vehicles described herein. For example, the microencapsulated delivery vehicles may include a heating agent, or a pharmaceutical such as a vitamin or a nutrient, or further, the microencapsulated delivery vehicles may include a UV absorber. A number of suitable active agents for incorporation into the microencapsulated delivery vehicles described herein are set forth below.

As noted above, the microencapsulated delivery vehicles as described herein may include a number of components and layers. Turning now to FIG. 1, there is shown a cross sectional view of a microencapsulated delivery vehicle 2 of the present disclosure. The microencapsulated delivery vehicle 2 includes a fugitive layer 4 surrounding a moisture protective layer 6 that surrounds an encapsulation layer 8. Additionally, microencapsulated delivery vehicle 2 includes an aqueous core composition 10 that includes a matrix material 100 and an active agent 12 surrounded by a hydrophobic wax material 14, and an encapsulating activator 16. Each of these layers and components, some of which are optional, are more thoroughly discussed below.

The microencapsulated delivery vehicles as described herein are desirably of a size such that, when incorporated into a personal care product such as a wet wipe, they cannot readily be felt on the skin by the user. Generally, the microencapsulated delivery vehicles have a diameter of from about 5 micrometers to about 10,000 micrometers, desirably from about 5 micrometers to about 5000 micrometers, desirably from about 50 micrometers to about 1000 micrometers, and still more desirably from about 300 micrometers to about 700 micrometers.

The aqueous core composition includes all of the components or materials that are encapsulated as described herein by, for example, a crosslinked polymeric system, to form the microencapsulated delivery vehicles. The aqueous core composition may include, for example, the matrix material (i.e., water), the active agent, a surfactant, an encapsulating activator, and a hydrophobic wax material that surrounds the active agent.

Typically, as discussed more fully below, the aqueous core composition is comprised substantially of water. In one embodiment, however, the aqueous core composition is not 100% aqueous, but can comprise an emulsion such as an oil-in-water emulsion or a water-in-oil emulsion. Furthermore, the aqueous core composition can be in the form of an oil, lotion, cream, or the like.

Generally, the aqueous core composition is present in the microencapsulated delivery vehicle in an amount of from about 1% (by weight microencapsulated delivery vehicle) to about 99.99% (by weight microencapsulated delivery vehicle), desirably from about 1% (by weight microencapsulated delivery vehicle) to about 95% (by weight microencapsulated delivery vehicle), more desirably from about 5% (by weight microencapsulated delivery vehicle) to about 90% (by weight microencapsulated delivery vehicle), more desirably from about 10% (by weight microencapsulated delivery vehicle) to about 90% (by weight microencapsulated delivery vehicle), more desirably from about 15% (by weight microencapsulated delivery vehicle) to about 80% (by weight microencapsulated delivery vehicle), and even more desirably from about 20% (by weight microencapsulated delivery vehicle) to about 70% (by weight microencapsulated delivery vehicle).

The matrix material included in the aqueous core composition is used as a carrying or bulking agent for other components of the microencapsulated delivery vehicle, including, for example, the active agent, the surfactant, and the encapsulating activator. Although generally preferred to be in liquid form, the matrix material may also be frozen and available in a substantially solid form as described more fully below. The matrix material is desirably an aqueous solution such as water. The matrix material is generally present in the aqueous core composition of the microencapsulated delivery vehicle in an amount of from about 60% (by weight aqueous core composition) to about 98% (by weight aqueous core composition), desirably from about 65% (by weight aqueous core composition) to about 85% (by weight aqueous core composition), more desirably from about 70% (by weight aqueous core composition) to about 80% (by weight aqueous core composition), and even more desirably about 75% (by weight aqueous core composition).

The microencapsulated delivery vehicle as disclosed herein also includes an active agent that is contained in the aqueous core composition. Typically, the active agent is soluble, dispersible, emulsifiable, and/or suspendable in water; that is, desirably, the active agent is dissolvable in the aqueous core composition. The active agent provides for a functional benefit such as skin conditioning when used in combination with a personal care product such as a wet wipe. Suitable active agents for use in the microencapsulated delivery vehicles include compounds that can provide a benefit to a location on or within a substrate. Suitable compounds for use as active agents in the aqueous core composition include, for example, skin care benefit agents, pharmaceuticals, xenobiotics, therapeutic agents, and combinations thereof. "Xenobiotics" is a general term used to describe any chemical interacting with an organism that does not occur in the normal metabolic pathways of that organism. Particularly preferred compounds include skin care benefit agents such as cleansing agents (e.g., tooth health agents, tooth whitening agents, enzymes), appearance modifying agents (e.g., exfoliation agents, skin-firming agents, anti-callous agents, anti-acne agents, anti-aging agents, anti-wrinkle agents), and surface conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs).

Additional pharmaceutical and therapeutic-type active agents for inclusion in the aqueous core composition include active agents such as neurosensory agents (e.g., agents that induce a perception of temperature change without involving an actual change in temperature such as, for example peppermint oil, eucalyptol, eucalyptus oil, methyl salicylate, camphor, tea tree oil, ketals, carboxamides, cyclohexanol derivatives, cyclohexyl derivatives, and combinations thereof), anti-dandruff agents, antiperspirant agents, wound care agents, enzyme agents, scar repair agents, colorant agents, humectant agents, hair care agents such as conditioners, styling agents, and detangling agents, powders, skin coloration agents such as tanning agents, lightening agents, and brightening agents, shine control agents and drugs, nutrients (e.g., anti-oxidants, transdermal drug delivery agents, botanical extracts, vitamins, magnets, magnetic metals, foods, and drugs), pesticides (e.g., tooth health ingredients, anti-bacterials, anti-virals, anti-fungals, preservatives, insect repellents, anti-acne agents, anti-dandruff agents, anti-parasite agents, wound care agents, and drugs), hair care agents (e.g., shaving lubricants, hair growth inhibitors, hair growth promoters, hair removers, anti-dandruff agents, colorant agents, humectants, hair care agents such as conditioners, styling agents, detangling agents, and drugs), anti-inflammatory agents (e.g., tooth health ingredients, skin conditioners, external analgesic agents, anti-irritant agents, anti-allergy agents, anti-inflammatory agents, wound care agents, transdermal drug delivery, and drugs), emotional benefit agents (e.g., gas generating agents, fragrances, odor neutralizing materials, exfoliation agents, skin-firming agents, anti-callous agents, anti-acne agents, anti-aging agents, soothing agents, calming agents, external analgesic agents, anti-wrinkle agents, anti-dandruff agents, antiperspirants, deodorants, wound care agents, scar care agents, coloring agents, powders, botanical extracts and drugs), indicators (e.g., soil indicators), and organisms.

In another embodiment, the active agent is a heating agent. The heating agent releases heat when contacted with water and may result in a warm feeling on the skin if used in combination with a personal care product such as a wet wipe. Suitable heating agents for use in the microencapsulated delivery vehicles include compounds with an exothermic heat of hydration and compounds with an exothermic heat of solution. Suitable compounds for use as heating agents in the aqueous core composition include, for example, calcium chloride, magnesium chloride, zeolites, aluminum chloride, calcium sulfate, magnesium sulfate, sodium carbonate, sodium sulfate, sodium acetate, metals, slaked lime, quick lime, glycols, and combinations thereof. The heating agents may be in either hydrous or anhydrous forms, although anhydrous forms are generally preferred. Particularly preferred compounds include magnesium chloride and calcium chloride. In another preferred embodiment, the heating agent is a heating gel such as commercially available K-Y® Brand Warming Ultragel. Typically, when the active agent is a heating agent, the heating agent is sufficiently surrounded by a hydrophobic wax material, as discussed more fully below, prior to being incorporated into the aqueous core composition.

Other additional suitable active agents include abrasive materials, abrasive slurries, acids, adhesives, alcohols, aldehydes, animal feed additives, antioxidants, appetite suppressants, bases, biocides, blowing agents, botanical extracts, candy, carbohydrates, carbon black, carbonless copying materials, catalysts, ceramic slurries, chalcogenides, colorants, cooling agents, corrosion inhibitors, curing agents, detergents, dispersants, EDTA, enzymes, exfoliation, fats, fertilizers, fibers, fire retardant materials, flavors, foams, food additives, fragrances, fuels, fumigants, gas forming compounds, gelatin, graphite, growth regulators, gums, herbicides, herbs, spices, hormonal based compounds, humectants, hydrides, hydrogels, imaging materials, ingredients that are easily oxidized or not UV stable, inks, inorganic oxides, inorganic salts, insecticides, ion exchange resins, latexes, leavening agents, liquid crystals, lotions, lubricants, maltodextrins, medicines, metals, mineral supplements, monomers, nanoparticles, nematicides, nicotine-based compounds, oil recovery agents, organic solvents, paint, peptides, pesticides, pet food additives, phase change materials, phase change oils, pheromones, phosphates, pigments, dyes, plasticizers, polymers, propellants, proteins, recording materials, silicates, silicone oils, stabilizers, starches, steroids, sugars, surfactants, suspensions, dispersions, emulsions, vitamins, warming materials, waste treatment materials, adsorbents, water insoluble salts, water soluble salts, water treatment materials, waxes, water, and yeasts.

The active agent is generally included in the aqueous core composition of the microencapsulated delivery vehicle in an amount of from about 0.01% (by weight aqueous core composition) to about 85% (by weight aqueous core composition), desirably from about 0.5% (by weight aqueous core composition) to about 50% (by weight aqueous core composition), more desirably from about 1% (by weight aqueous core composition) to about 30% (by weight aqueous core composition), and even more desirably about 20% (by weight aqueous core composition).

The active agent utilized in the microencapsulated delivery vehicle generally has a particle size of from about 0.01 micrometers to about 4000 micrometers, desirably from about 10 micrometers to about 1000 micrometers, desirably from about 10 micrometers to about 500 micrometers, and more desirably from about 10 micrometers to about 100 micrometers to facilitate substantial and continuous release of the functional benefit. In one specific embodiment, a particle size of from about 149 micrometers to about 355 micrometers is preferred. Although many active agents as described herein are commercially available in a number of particle sizes, it will be recognized by one skilled in the art that any number of techniques can be used to grind and produce the desired particle sizes.

Along with the active agent, a surfactant may optionally be included in the aqueous core composition. As used herein, "surfactant" is intended to include surfactants, dispersants, gelling agents, polymeric stabilizers, structurants, structured liquids, liquid crystals, rheological modifiers, grinding aids, defoamers, block copolymers, and combinations thereof. If a surfactant is utilized, it should be substantially non-reactive with the active agent. A surfactant may be added along with an active agent and matrix material to the aqueous core composition as a grinding and mixing aid for the active agent and to reduce the surface tension of the aqueous core composition. In one embodiment, the use of a surfactant in the aqueous core composition generally allows for higher loading of the active agent within the aqueous core composition without unwanted flocculation of the active material occurring, which can hinder the release of the active agent onto the surface of the product.

Any one of a number of surfactant types including anionic, cationic, nonionic, zwitterionic, and combinations thereof can be utilized in the aqueous core composition. One skilled in the art will recognize, based on the disclosure herein, that different active agents may benefit from one type of surfactant more than another; that is, the preferred surfactant for one chemistry may be different than the preferred surfactant for another. Particularly desirable surfactants will allow the aqueous core composition including the matrix material, active agent, and surfactant mixture to have a suitable viscosity for thorough mixing; that is, the surfactant will not result in the mixture having an undesirably high viscosity.

When included in the aqueous core composition of the microencapsulated delivery vehicles of the present disclosure, the surfactant is generally present in an amount of from about 0.01% (by weight aqueous core composition) to about 40% (by weight aqueous core composition), desirably from about 0.1% (by weight aqueous core composition) to about 25% (by weight aqueous core composition), more desirably from about 0.1% (by weight aqueous core composition) to about 10% (by weight aqueous core composition), more desirably from about 1% (by weight aqueous core composition) to about 5% (by weight aqueous core composition), and still more desirably about 1% (by weight aqueous core composition).

The aqueous core composition can further optionally include a viscosity increasing agent. By increasing the viscosity of the aqueous core composition (i.e., matrix material and active agent), the active agent is less likely to prematurely leak from the microencapsulated delivery vehicle into the product and possibly react with the other components of the product, such as the wetting solution of a wet wipe. Furthermore, by increasing the viscosity of the aqueous core composition, the aqueous core composition can more easily be encapsulated with the encapsulation layer.

Suitable viscosity increasing agents include aqueous viscosity increasing agents, for example, acetamide MEA, acrylamide copolymers, acrylamide/sodium acrylate copolymer, acrylamide/sodium acryloyldimethyltaurate copolymer, acrylates/acetoacetoxyethyl methacrylate copolymer, acrylates/beheneth-25 methacrylate copolymer, acrylates/C10-C30 alkyl acrylate crosspolymer, actylates/ceteth-20 itaconate copolymer, acrylates/ceteth-20 methacrylate copolymer, actylates/laureth-25 methacrylate, acrylates/pameth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylic acid/acrylonitrogens copolymer, adipic acid/methyl DEA crosspolymer, agar, agarose, *alcaligenes* polysaccharides, algin, alginic acid, almondamide DEA, almondamidopropyl betaine, aluminum/magnesium hydroxide stearate, ammonium acrylates/acrylonitrogens copolymer, ammonium acrylates copolymer, ammonium acryloyldimethyltaurate/vinyl formamide copolymer, ammonium acryloyldimethyltaurate/VP copolymer, ammonium alginate, ammonium chloride, ammonium polyacryloyldimethyl taurate, ammonium sulfate, amylopectin, apricotamide DEA, apricotamidopropyl betaine, arachidyl alcohol, arachidyl glycol, *Arachis hypogaea* (Peanut) flour, ascorbyl methylsilanol pectinate, *astragalus* gummifer gum, attapulgite, *Avena sativa* (Oat) kernel flour, avocadamide DEA, avocadamidopropyl betaine, azelamide MEA, babassuamide DEA, babassuamide MEA, babassuamidopropyl betaines, behenamide DEA, behenamide MEA, behenamidopropyl betaine, behenyl betaine, bentonite, butoxy chitosan, caesalpinla spinosa gum, calcium alginate, calcium carboxymethyl cellulose, calcium carrageenan, calcium chloride, calcium potassium carbomer, calcium starch octenylsuccinate, C20-C40 alkyl stearate, canolamidopropyl betaine, capramide DEA, capryl/capramidopropyl betaine, carbomer, carboxybutyl chitosan, carboxymethyl cellulose acetate butyrate, carboxymethyl chitin, carboxymethyl chitosan, carboxymethyl dextran, carboxymethyl hydroxyethylcellulose, carboxymethyl hydroxypropyl guar, carnitine, cellulose acetate propionate carboxylate, carnitine, cellulose acetate propionate carboxylate, cellulose gum, ceratonia siliqua gum, cetearyl alcohol, cetyl alcohol, cetyl babassuate, cetyl betaine, cetyl glycol, cetyl hydroxyethylcellulose, chimyl alcohol, cholesterol/HDI/pullulan copolymer, cholesteryl hexyl dicarbamate pullulan, citrus *Aurantium dulois* (Orange) peel extract, cocamide DEA, cocamide MEA, cocamide MIPA, cocamidoethyl betaine, cocamidopropyl betaine, cocamidopropyl hydroxysultaine, coco-betaine, coco-hydroxysultaine, coconut alcohol, coco/oleamidopropyl betaine, coco-sultaine, cocoyl sarcosinamide DEA, cornamide/cocamide DEA, cornamide DEA, croscarmellose, *cyamopsis tetragonoloba* (guar) gum, decyl alcohol, decyl betaine, dehydroxanthan gum, dextrin, dibenzylidene sorbitol, diethanolaminooleamide DEA, diglycol/CHDM/isophthalates/SIP copolymer, dihydroabietyl behenate, dihydrogenated tallow benzylmonium hectorite, dihydroxyaluminum aminoacetate, dimethicone/PEG-15 crosspolymer, dimethicone propyl PG-betaine, DMAPA acrylates/acrylic acid/acrylonitrogens copolymer, erucamidopropyl hydroxysultaine, ethylene/sodium acrylate copolymer, gelatin, gellan gum, glyceryl alginate, glycine soja (Soybean) flour, guar hydroxypropyltrimonium chloride, hectorite, hyluronic acid, hydrated silica, hydrogenated potato starch, hydrogenated tallow, hydrogenated tallowamide DEA, hydrogenated tallow betaine, hydroxybutyl methylcellulose, hydroxyethyl acrylate/sodium acryloyldimethyl taurate copolymer, hydroxyethylcellulose, hydroxyethyl chitosan, hydroxyethyl ethylcellulose, hydroxyethyl stearamide-MIPA, hydroxylauryl/hydroxymyristyl betaine, hydroxypropylcellulose, hyroxypropyl chitosan, hydroxylpropyl ethylenediamine carbomer, hydroxypropyl guar, hydroxylpropyl methylcellulose, hydroxylpropyl methylcellulose stearoxy ether, hydroxypropyl starch, hydroxypropyl starch phosphate, hydroxypropyl xanthan gum, hydroxystearamide DEA, isobutylene/sodium maleate copolymer, isostearamide DEA, isostearamide MEA, isostearmaide MIPA, isostearmidopropyl betaine, lactamide MEA, lanolinamide DEA, lauramide DEA, lauramide MEA, lauramide MIPA, lauramide/myristamide DEA, lauramidopropyl betaine, lauramidopropyl hydroxysultaine, lauramino bispropanediol, lauryl alcohol, lauryl betaine, lauryl hydroxysultaine, lauryl sultaine, lecithinamide DEA, linoleamide DEA, linoleamide MEA, linoleaide MIPA, lithium magnesium silicate, lithium magnesium sodium silicate, *Macrocystis pyrifera* (Kelp), magnesium alginate, magnesium/aluminum/hydroxide/carbonate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, milkamidopropyl betaine, minkamide DEA, minkamidopropyl betaine, MIPA-myristate, montmorillonite, moroccan lava clay, myristamide DEA, myristamide MEA, myristamide MIPA, myristamidopropyl betaine, myristamidopropyl hydroxysultaine, myristyl alcohol, myristyl betaine, natto gum, nonoxynyl hydroxylethylcellulose, oatamide MEA, oatamidopropyl betaine, octacosanyl glycol isostearate, octadecene/ma copolymer, oleamide DEA, oleamide MEA, oleamide MIPA, oleamidopropyl betaine, oleamidopropyl hydroxysultaine, oleyl betaine, olivamide DEA, olivamidopropyl hydroxysultaine, oliveamide MEA, palmamide DEA, palmamide MEA, palmamide MIPA, palmamidopropyl betaine, palm kernel alcohol, palm kernelamide DEA, palm kernelamide MEA, palm kernelamide MIPA, palm kernelamidopropyl betaine, peanutamide MEA, peanutamide MIPA, pectin, PEG-800, PEG-crosspolymer, PEG-150/decyl alcohol/SMDI copolymer, PEG-175 dilsostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14M, PEG-20M, PEG-23M, PEG-25, PEG-45M, PEG-65M, PEG-90M, PEG-115M, PEG-160M, PEG-120 methyl glucose trioleate, PEG-180/octoxynol-4/TMMG copolymer, PEG-150 pentaerythrityl tetrastearate, PEG-4 rapeseedamide, PEG-150/stearyl alcohol/SMDI copolymer, *Phaseolus anguilaris* seed powder, *Polianthes tuberosa* extract, polyacrylate-3, polyacrylic acid, polycyclopentadiene, polyether-1, polyethylene/isopropyl maleate/MA copolyol, polyglyceryl-3 disiloxane dimethicone, polyglyceryl-3 polydimethylsiloxyethyl dimethicone, polymethacrylic acid, pokyquaternium-52, polyvinyl alcohol, potassium alginate, potassium aluminum polyacrylate, potassium carbomer, potassium carrageenan, potassium chloride, potassium palmate, potassium polyacrylate, potassium sulfate, potato starch modified, PPG-2 cocamide, PPG-1 hydroxyethyl caprylamide, PPG-2 hydroxyethyl cocamide, PPG-2 hydroxyethyl coco/isostearamide, PPG-3 hydroxyethyl soyamide, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, *Pyrus cyclonia* seed, *Pyrus malus* (Apple) fiber, rhizobian gum, ricebranamide DEA, ricinoleamide DEA, ricinoleamide MEA, ricinoleamide MIPA, ricinoleamidopropyl betaine, ricinoleic acid/adipic acid/AEEA copolymer, *rosa* multiflora flower was, sclerotium gum, sesamide DEA, sesamidopropyl betaine, sodium acrylate/acryloyldimethyl taurate copolymer, sodium acrylates/acrolein copolymer, sodium acrylates/acrylonitrogens copolymer, sodium acrylates copolymer, sodium acrylates crosspolymer, sodium acrylates/vinyl isodecanoate crosspolymer, sodium acrylate/vinyl alcohol copolymer, sodium carbomer, sodium carboxymethyl chitin, sodium carboxymethyl dextran, sodium carboxymethyl beatglucan, sodium carboxymethyl starch, sodium carrageenan, sodium cellulose sulfate, sodium chloride, sodium cyclodextrin sulfate, sodium hydroxypropyl starch phosphate, sodium isooctylene/MA copolymer, sodium magnesium fluorosilicate, sodium oleate, sodium palmitate, sodium palm kernelate, sodium polyacrylate, sodium polyacrylate starch, sodium polyacryloyldimethyl taurate, sodium polygammaglutamate, sodium polymethyacrylate, sodium polystyrene sulfonate, sodium silicoaluminate, sodium starch octenylsuccinate, sodium stearate, sodium stearoxy PG-hydroxyethylcellulose sulfonate, sodium styrene/acrylates copolymer, sodium sulfate, sodium tallowate, sodium tauride acrylates/acrylic acid/acrylonitrogens copolymer, sodium tocopheryl phosphate, *Solanum tuberosum* (potato) starch soyamide DEA, soyamidopropyl betaine, starch/acrylates/acrylamide copolymer, starch hydroxypropyltrimonium chloride, stearamide AMP stearamide DEA, stearamide DEA-distearate, stearamide DIBA-stearate, stearamide MEA, stearamide MEA-stearate, stearamide MIPA, stearamidopropyl betaine, steareth-60 cetyl ether, steareth-100/PEG-136/HDI copolymer, stearyl alcohol, stearyl betaine, *Sterculia urens* gum, synthetic fluorphlogopite, tallamide DEA, tallow alcohol, tallowamide DEA, tallowamide MEA, tallowamidopropyl betaine, tallowamidopropyl hydroxysultaine, tallowamine oxide, tallow betaine, tallow dihydroxyethyl betaine, *Tamarindus indica* seed gum, tapioca starch, TEA-alginate, TEA-carbomer, TEA-hydrochlorite, trideceth-2 carboxamide MEA, tridecyl alcohol, triethylene glycol dibenzoate, trimethyl pentanol hydroxyethyl ether, *triticum vulgare* (Wheat) germ powder, *triticum vulgare* (Wheat) kernel flour, *triticum vulgare* (Wheat) starch, tromethamine acrylates/acrylonitrogens copolymer, tromethamine magnesium aluminum silicate, undecyl alcohol, undecyulenamide DEA, undecylenamide MEA, undecylenamdopropyl betaine, welan gum, wheat germamide DEA, wheat germamidopropyl betaine, xanthan gum, yeast beta-glucan, yeast polysaccharides, *Zea mays* (Corn) starch, and combinations thereof. Particularly preferred viscosity increasing agents include fumed silica and laponite clay.

The viscosity increasing agents are suitably present in the aqueous core composition in an amount of from about 0.2% (by weight aqueous core composition) to about 15% (by weight aqueous core composition). More suitably, the viscosity increasing agents are present in the aqueous core composition in an amount of from about 1% (by weight aqueous core composition) to about 10% (by weight aqueous core composition), and even more suitably, about 6.3% (by weight aqueous core composition).

In another embodiment, the viscosity of the aqueous core composition can be increased by freezing the matrix material (i.e., water). Specifically, the matrix material is suitably frozen to produce a solid matrix material. For example, when the matrix material is water, the aqueous core composition includes solid ice as the matrix material.

Any suitable method of freezing the matrix material can be used in the present disclosure. For example, in one embodiment, the matrix material is refrigerated at a temperature of about −10° C. (14° F.) for approximately 60 minutes to freeze the matrix material. In another embodiment, the matrix material is frozen using an excess of liquid nitrogen. For example, in one particularly preferred embodiment, the matrix material is frozen using nitrogen in a weight ratio of matrix material to nitrogen of from about 1:100 to about 1:500. More suitably, the matrix material is frozen using nitrogen in a weight ratio of matrix material to nitrogen of from about 1:150 to about 1:350, even more suitably 1:250.

A suitably viscosity for the aqueous core composition can be determined using yield stress. The yield stress is the amount of force necessary to deform the aqueous core composition. Yield stress of the aqueous core composition can be measured using methods familiar to those with ordinary skill in the art as described below.

Yield Stress:

A rheometer with a 4-centimeter diameter parallel plate geometry at a gap setting of 1 millimeter, for example a TA Instruments AR 2000 controlled stress rheometer manufactured by TA Instruments-Waters LLC, New Castle, Del., 19720, is used. A sample of aqueous core composition is loaded onto the rheometer base plate at 25° C., and the upper plate is positioned at a distance 1 millimeter from the base plate, containing the aqueous core composition between the plates. Without disturbing the core composition, excess is removed to the edge of the plate with a spatula. Using a controller and a computer (provided with rheometer), the rheometer is programmed to increase stress on the sample from a starting value of 0.1 Pascals (Pa) to a final value of 1,000 Pa in a series of 50 steps per decade of stress at a logarithmic rate of increase, over a total measurement time of 3 minutes. Data are collected in an electronic file for analysis. First, data are plotted as the log of stress/Pa vs. log of strain, and the yield stress is determined. The yield stress, or stress at which product flow begins, is the point at which the data exhibit a transition from non-flow into flow, evident as a kink in the curve of the log stress vs. log strain curve. Data in the non-flow region are linearized by regression or simply drawing a straight line through the non-flow data; and data in the flow region are linearized by regression or drawing a similar straight line, and the intersection of the linear regressions or the straight lines is determined to be the yield stress. For preferred products, a pronounced yield stress is demonstrated as a sharp bend in the data curves at the yield stress, as the composition rapidly shifts from non-flow to flow with increasing stress. For compositions that do not exhibit a yield stress by this method, the yield stress is taken to be a low value, i.e., less than 1 Pa or even 0 Pa for fluids such as Newtonian fluids.

Suitably, the viscosity of the aqueous core composition is increased such that the yield stress of the aqueous core compositions is at least about 5 Pa. More suitably, the yield stress of the aqueous core composition is at least about 10 Pa, even more suitably, at least about 15 Pa, and even more suitably, at least about 20 Pa.

As will be described in more detail below, during the manufacturing process for a product incorporating the microencapsulated delivery vehicle, the encapsulated aqueous core composition including the matrix material and the active agent is combined with other components of the product. During production with these other components, it may be possible for the active agent present in the aqueous core composition to come into contact with another component and react, prematurely generating a benefit sensation. This contact can result in a loss of potency and deactivation of the active agent and render the resulting microencapsulated delivery vehicle ineffective for its intended purpose. As such, in one embodiment of the present disclosure, the active agent included in the aqueous core composition is substantially completely surrounded by a hydrophobic wax material prior to being introduced into the aqueous core composition and ultimately into the product. This hydrophobic wax material may provide the active agent with temporary protection during the timeframe of manufacturing, transportation, and storage of the product; that is, the hydrophobic wax material may keep the additional components of the product from contacting the active agent.

In an alternative embodiment, the hydrophobic wax material does not substantially dissolve into the aqueous core composition and off of the active agent but is removed from the active agent at the time of use through shearing or disruption of the hydrophobic wax material; that is, the hydrophobic wax material is mechanically broken off of the active agent to allow the active agent access to the surrounding environment.

It is generally desirable to have substantially complete coverage of the active agent with the hydrophobic wax material to ensure that the active agent is not susceptible to contact with other components during the incorporation of the aqueous core composition, and ultimately the microencapsulated delivery vehicle, into a product as described herein. When contacted with a substantially continuous layer of hydrophobic wax material, the aqueous core composition including the matrix material and the active agent can be encapsulated in the liquid environment without the active agent losing potency. Generally, the hydrophobic wax material may be applied to the active agent in from about 1 to about 30 layers, desirably in from about 1 to about 10 layers.

Generally, the hydrophobic wax material is present on the active agent in an amount of from about 1% (by weight active agent) to about 50% (by weight active agent), desirably from about 1% (by weight active agent) to about 40% (by weight active agent), more desirably from about 1% (by weight active agent) to about 30% (by weight active agent), and even more desirably from about 1% (by weight active agent) to about 20% (by weight active agent). At these levels, there is sufficient hydrophobic wax material present on the active agent to provide the desired level of protection.

Suitable hydrophobic wax materials for coating the active agent are relatively low temperature melting wax materials. Although other hydrophobic low temperature melting materials can be used to coat the active agent in accordance with the present disclosure, low temperature melting hydrophobic wax materials are generally preferred. In one embodiment, the hydrophobic wax material has a melting temperature of less than about 140° C., desirably less than about 90° C. to facilitate the coating of the heating agent as described below.

Suitable hydrophobic wax materials for use in coating the active agent include, for example, organic ester and waxy compounds derived from animal, vegetable, and mineral sources including modifications of such compounds in addition to synthetically produced materials having similar properties. Specific examples that may be used alone or in combination include glyceryl tristearate, glyceryl distearate, canola wax, hydrogenated cottonseed oil, hydrogenated soybean oil, castor wax, rapeseed wax, beeswax, carnauba wax, candelilla wax, microwax, polyethylene, polypropylene, epoxies, long chain alcohols, long chain esters, long chain fatty acids such as stearic acid and behenic acid, hydrogenated plant and animal oils such as fish oil, tallow oil, and soy oil, microcrystalline waxes, metal stearates and metal fatty acids. Specific commercially available hydrophobic wax materials include, for example, Dynasan™ 110, 114, 116, and 118 (commercially available from DynaScan Technology Inc., Irvine, Calif.), Sterotex™ (commercially available from ABITEC Corp., Janesville, Wis.); Dritex C (commercially available from Dritex International, LTD., Essex, U.K.); Special Fat™ 42, 44, and 168T.

As noted herein, the microencapsulated delivery vehicles include an encapsulation layer that substantially completely surrounds the aqueous core composition that includes the encapsulating activator (as discussed below), matrix material, active agent, and optionally the hydrophobic wax material and the surfactant. The encapsulation layer allows the aqueous core composition including the active agent to undergo further processing and use without a loss of structural integrity; that is, the encapsulation layer provides structural integrity to the aqueous core composition and its contents to allow for further processing.

Although described in more detail below, and generally in relation to a crosslinked polymeric material, the encapsulation layer may be comprised of a polymeric material, a crosslinked polymeric material, or a combination thereof, that results in a shell material that may be formed during manufacturing. Specifically, the encapsulation layer may be comprised of crosslinked sodium alginate, anionic dispersed latex emulsions, crosslinked polyacrylic acid, crosslinked polyvinyl alcohol, crosslinked polyvinyl acetate, carbonates, sulfates, phosphates, borates, polyvinyl pyrolidone, PLA/PGA, crosslinked starch, nylon, ureas, hydrocolloids, clays, and combinations thereof. One particularly preferred crosslinked polymeric system is crosslinked sodium alginate.

The encapsulation layer present in the microencapsulated delivery vehicle generally has a thickness of from about 0.1 micrometers to about 500 micrometers, desirably from about 1 micrometer to about 80 micrometers, more desirably from about 1 micrometer to about 50 micrometers, more desirably from about 1 micrometer to about 20 micrometers, and even more desirably from about 10 micrometers to about 20 micrometers. At these thicknesses, the crosslinked polymeric layer has a sufficient thickness to provide its intended function. The encapsulation layer may be one discrete layer, or may be comprised of multiple layers added in one or more steps. Suitable methods for measuring the thickness of the encapsulation layer (once fractured), and the other optional layers described herein, include Scanning Electron Microscopy (SEM) and Optical Microscopy.

Generally, the encapsulation layer will be present in from about 1 layer to about 30 layers, desirably in from about 1 layer to about 20 layers, and more desirably in from about 1 layer to about 10 layers to provide further protection.

The encapsulation layer is generally present in the microencapsulated delivery vehicle in an amount of from about 0.001% (by weight microencapsulated delivery vehicle) to about 99% (by weight microencapsulated delivery vehicle), desirably from about 0.1% (by weight microencapsulated delivery vehicle) to about 90% (by weight microencapsulated delivery vehicle), more desirably from about 1% (by weight microencapsulated delivery vehicle) to about 75% (by weight microencapsulated delivery vehicle), more desirably from about 1% (by weight microencapsulated delivery vehicle) to about 50% (by weight microencapsulated delivery vehicle), more desirably from about 1% (by weight microencapsulated delivery vehicle) to about 20% (by weight microencapsulated delivery vehicle), and still more desirably about 1% (by weight microencapsulated delivery vehicle).

The microencapsulated delivery vehicle as described herein may optionally comprise a moisture protective layer to produce a substantially fluid-impervious microencapsulated delivery vehicle. As used herein, "fluid" is meant to include both water (and other fluids) and oxygen (and other gases) such that "fluid-impervious" includes both water-impervious and oxygen-impervious. Although referred to throughout herein as a "moisture protective layer," one skilled in the art based on the disclosure herein will recognize that this layer may be both "moisture protective" and "oxygen protective;" that is, the layer will protect and insulate the aqueous core composition and its contents from both water and oxygen.

When present, the moisture protective layer substantially completely surrounds the crosslinked polymeric encapsulation layer described above. The moisture protective layer will help to ensure that the microencapsulated composition and its contents (e.g., active agent) will not come into contact with the other components of the product (e.g., wetting solution of a wet wipe) and, ultimately, allow for premature release of the active agent and generation of the benefit of the active agent. Furthermore, the moisture protective layer will ensure that the aqueous core composition does not evaporate into the product; that is, the moisture protective layer prevents water from the aqueous core composition from leaking out of the microencapsulated delivery vehicle into the product.

The moisture protective layer may be present on the microencapsulated delivery vehicle in one layer or in multiple layers. Desirably, the moisture protective layer will be present in from about 1 layer to about 30 layers, desirably in from about 1 layer to about 20 layers, and more desirably in from about 1 layer to about 10 layers to provide further protection. As noted above, the moisture protective layer substantially completely surrounds the encapsulating layer to prevent the active agent from leaking. To ensure the moisture protective layer substantially completely covers the encapsulating layer, multiple layers may be utilized as noted above. Each of the moisture protective layers generally has a thickness of from about 1 micrometer to about 200 micrometers, desirably from about 1 micrometer to about 100 micrometers, and even more desirably from about 1 micrometer to about 50 micrometers.

The moisture protective layer may comprise any number of materials including, for example, polyols in combination with isocynate, styrene-acrylate, vinyl toluene-acrylate, styrene-butadiene, vinyl-acrylate, polyvinyl butyral, polyvinyl acetate, polyethylene terephthalate, polypropylene, polystyrene, polymethyl methacrylate, poly lactic acid, polyvinylidene chloride, polyvinyldichloride, polyethylene, alkyl polyester, carnauba wax, hydrogenated plant oils, hydrogenated animal oils, fumed silica, silicon waxes, fluorinated chlorosilanes, ethoxy fluorochemicals, methoxyfluorochemicals, titanium dioxide, silicon dioxide, metals, metal carbonates, metal sulfates, ceramics, metal phosphates, microcrystalline waxes, and combinations thereof.

Generally, the moisture protective layer is present in the microencapsulated delivery vehicle in an amount of from about 0.001% (by weight microencapsulated delivery vehicle) to about 99.8% (by weight microencapsulated delivery vehicle), desirably from about 0.1% (by weight microencapsulated delivery vehicle) to about 90% (by weight microencapsulated delivery vehicle), more desirably in an amount of from about 1% (by weight microencapsulated delivery vehicle) to about 75% (by weight microencapsulated delivery vehicle), more desirably in an amount of from about 1% (by weight microencapsulated delivery vehicle) to about 50% (by weight microencapsulated delivery vehicle), and even more desirably in an amount of from about 5% (by weight microencapsulated delivery vehicle) to about 35% (by weight microencapsulated delivery vehicle).

In addition to the moisture protective layer, the microencapsulated delivery vehicle may also optionally include a fugitive layer that surrounds the moisture protective layer, if present, or the encapsulating layer if the moisture protective layer is not present. The fugitive layer can act to stabilize and protect the microencapsulated delivery vehicle from rupturing prematurely due to mechanical load, or can provide other benefits. When present on the microencapsulated delivery vehicle, the fugitive layer can impart strength and withstand a given mechanical load until a time when the fugitive layer is ruptured by the end user or is decomposed or degraded in a predictable manner in a wet wipe solution, usually during shipment and/or storage of the product prior to use. Consequently, the fugitive layer allows the microencapsulated delivery vehicle to survive relatively high mechanical load conditions commonly experienced in shipping and/or manufacturing.

In one embodiment, the fugitive layer substantially completely surrounds the moisture protective layer (or the encapsulating layer) such that there are substantially no access points to the underlying layer. Alternatively, the fugitive layer may be a non-continuous, porous or non-porous layer surrounding the moisture protective layer (or the encapsulating layer).

The fugitive layer, similar to the moisture protective layer, may be present in multiple layers. Specifically, the fugitive layer may be present in anywhere from about 1 to about 30 layers, desirably from about 1 to about 20 layers, and more desirably from about 1 to about 10 layers. Generally, each fugitive layer may have a thickness of from about 1 micrometer to about 200 micrometers, desirably from about 1 micrometer to about 100 micrometers, and more desirably from about 1 micrometer to about 50 micrometers.

The fugitive layer is generally present in the microencapsulated delivery vehicle in an amount of from about 0.001% (by weight microencapsulated delivery vehicle) to about 99.8% (by weight microencapsulated delivery vehicle), desirably in an amount of from about 0.1% (by weight microencapsulated delivery vehicle) to about 90% (by weight microencapsulated delivery vehicle), more desirably in an amount of from about 1% (by weight microencapsulated delivery vehicle) to about 80% (by weight microencapsulated delivery vehicle), more desirably in an amount of from about 1% (by weight microencapsulated delivery vehicle) to about 75% (by weight microencapsulated delivery vehicle), and even more desirably in an amount of from about 1% (by weight microencapsulated delivery vehicle) to about 50% (by weight microencapsulated delivery vehicle).

The fugitive layer may be comprised of any one of a number of suitable materials including, for example, polymers of dextrose, sugars, starches, alginate, acrylates, polyvinyl alcohol, gum arabic, polyacrylamide, hydroxypropyl cellulose, hydroxypropyl methylcellulose, polyvinyl pyrrolidone, poly (2-acrylamido-2-methyl-1-propanesulfonic acid), poly(acrylamido-N-propyltrimethylammonium chloride), and combinations thereof. One particularly preferred material for use as the fugitive layer is starch.

The microencapsulated delivery vehicles as described herein may be manufactured in any number of ways as discussed below. The first step in the manufacturing process is generally to coat the desired delivery vehicle (i.e., active agent) with a hydrophobic wax material as described above prior to incorporating the hydrophobic wax material-coated active agent into the aqueous core composition. As would be recognized by one skilled in the art based on the disclosure herein, this hydrophobic wax material coating of the active agent step is optional and can be eliminated if such a coating is not desired and the active agent is to be incorporated into the aqueous core composition without any protective coating.

In one embodiment, the hydrophobic wax material is coated onto the active agent by blending the active agent and hydrophobic wax material together at an elevated temperature sufficient to melt the hydrophobic wax material in the presence of the active agent and the melted wax material and active agent stirred sufficiently to coat the active agent. After the coating of the active agent is complete, the mixture is allowed to cool to room temperature to allow the wax to solidify on the active agent particles. After the coated active agent particles have cooled, they can be ground to the desired size prior to incorporation into the matrix material.

After the grinding of the hydrophobic wax material-coated active agent, it may be desirable to subject the ground material to a further process to ensure that the hydrophobic wax material coating is substantially complete around the active agents. Suitable additional processes include, for example, spheroidization (high heat fluidization slightly below the melt temperature of the hydrophobic wax material) and ball milling. These additional processes can be used to ensure substantially complete coverage of the active agent with the hydrophobic wax material.

In preparing the microencapsulated delivery vehicle, an aqueous core composition including the hydrophobic wax material-coated (or uncoated) active agent, an encapsulating activator, and surfactant (if utilized) are first mixed together with the matrix material. This aqueous core composition is the resulting "core material" inside of the encapsulating layer (s), although it will be recognized by one skilled in the art based on the disclosure herein that the encapsulating activator, if initially present in the aqueous core composition, may be substantially or completely used up in the crosslinking reaction described herein. As will be further recognized by one skilled in the art, some methods of forming an outer layer on the aqueous core composition (i.e., coacervation) may not require a chemical encapsulating activator to be present in the aqueous core composition, but may utilize a change in pH, a change in temperature, and/or a change in ionic strength of the liquid solution to initiate the formation of the encapsulating layer around the aqueous core composition. Additionally, it will be further recognized by one skilled in the art based on the disclosure herein that the encapsulating activator, when present, may be located outside of the aqueous core composition; that is, the encapsulating activator may be located in the liquid solution for example, although it is generally desirable to have it located within the aqueous core composition.

The encapsulating activator, when present in the aqueous core composition, acts as a crosslinking agent to crosslink the encapsulating layer discussed herein. Once the aqueous core composition is introduced into a liquid solution containing a crosslinkable compound as described below, the encapsulating activator interacts with the crosslinkable compound and causes it to crosslink on the outer surface of the composition to form a crosslinked shell. Because the encapsulating activator chemically reacts with the crosslinkable compound contained in the liquid solution, the resulting microencapsulated delivery vehicle may not contain any encapsulating activator in its final form; or, it may contain a small amount of encapsulating activator not consumed in the crosslinking reaction, which in some cases may then act as an additional active agent.

The encapsulating activator may be any activator capable of initiating a crosslinking reaction in the presence of a crosslinkable compound. Suitable encapsulating activators include, for example, polyvalent ions of calcium, polyvalent ions of copper, polyvalent ions of barium, silanes, aluminum, titanates, chelators, acids, and combinations thereof. Specifically, the encapsulating activator may be calcium chloride, calcium sulfate, calcium oleate, calcium palmitate, calcium stearate, calcium hypophosphite, calcium gluconate, calcium formate, calcium citrate, calcium phenylsulfonate, and combinations thereof. A preferred encapsulating activator is calcium chloride.

The encapsulating activator is generally present in the aqueous core composition in an amount of from about 0.1% (by weight aqueous core composition) to about 25% (by weight aqueous core composition), desirably from about 0.1% (by weight aqueous core composition) to about 15% (by weight aqueous core composition), and still more desirably from about 0.1% (by weight aqueous core composition) to about 10% (by weight aqueous core composition).

One skilled in the art will recognize based on the disclosure herein that the encapsulating activator may be the same chemical compound as the active agent; that is, the same chemical compound may act as both the encapsulating activator and the active agent. When a single compound is to function as both active agent and encapsulating activator, an increased amount is utilized in the composition to ensure there is sufficient compound remaining after the crosslinking reaction to function as the active agent. Of course, if a single compound is to function as both active agent and encapsulating activator, a portion of the compound may be surrounded as described herein by a hydrophobic wax material prior to incorporation into the composition. This protected portion of the dual function compound would not be available in this embodiment to act as an encapsulating activator.

To produce the aqueous core composition including the matrix material, active agent (which may or may not be surrounded by a hydrophobic wax material), encapsulating activator and surfactant (if any), the desired amounts of these components may be optionally passed through a milling device that serves to thoroughly mix the components together for further processing. Suitable wet milling operations include, for example, bead milling and wet ball milling. Additionally, processes known to those skilled in the art such as hammer milling and jet milling may be used to first prepare the active agent, and then disperse the treated active agent into the matrix material containing the surfactant and encapsulating activator followed by thorough mixing.

Once the aqueous core composition is prepared, it is introduced into a liquid solution, generally held at room temperature, to activate a crosslinking reaction to form an outer encapsulating shell that protects the aqueous core composition and its components (core material) and allows for immediate use or further processing. Although described herein primarily in reference to a "crosslinking reaction," it will be recognized by one skilled in the art based on the disclosure herein that the encapsulation layer can be formed around the aqueous core composition not only by a crosslinking reaction, but also by coacervation, coagulation, flocculation, adsorption, complex coacervation and self-assembly, all of which are within the scope of the present disclosure. As such, the term "crosslinking reaction" is meant to include these other methods of forming the encapsulation layer around the aqueous core composition.

One particular advantage of one embodiment described herein is that the presence of the encapsulating activator in the aqueous core composition allows for almost instantaneous crosslinking when the aqueous core composition is introduced into the solution containing the crosslinkable compound; this reduces the potential for unwanted active agent deactivation. In one embodiment, the aqueous core composition is added dropwise into the liquid containing the crosslinkable compound and the robust beads that form when the drops contact the liquid are kept separated during the crosslinking reaction using a sufficient amount of stirring and mixing. It is preferred to use sufficient stirring and mixing to keep the beads separate during the crosslinking reaction to ensure that they remain separate, individual beads and do not form larger agglomerated masses that are susceptible to numerous defects. Generally, the drops added to the liquid solution can have a diameter of from about 0.05 millimeters to about 10 millimeters, desirably from about 1 millimeter to about 3 millimeters, and still more desirably from about 0.5 millimeters to about 1 millimeter.

In one embodiment, the liquid solution includes a crosslinkable compound that can be crosslinked in the presence of the encapsulating activator to form the outer encapsulate shell. Optionally, a surfactant as described herein can also be introduced into the liquid solution to facilitate crosslinking. When the aqueous core composition including the encapsulating activator is introduced into the liquid containing the crosslinkable compound, the encapsulating activator migrates to the interface between the aqueous core composition and the liquid solution and initiates the crosslinking reaction on the surface of the aqueous core composition to allow the encapsulation layer to grow outward toward the liquid solution. The thickness of the resulting encapsulation layer surrounding the aqueous core composition can be controlled by (1) controlling the amount of encapsulating activator included in the aqueous core composition; (2) controlling the amount of time the aqueous core composition including the encapsulating activator is exposed to the liquid solution including the crosslinkable compound; and/or (3) controlling the amount of crosslinkable compound in the liquid solution. Generally, an encapsulating layer of sufficient and desired thickness can be formed around the aqueous core composition by allowing the aqueous core composition to dwell in the liquid solution including the crosslinkable compound for from about 10 seconds to about 40 minutes, desirably from about 15 seconds to about 30 minutes, and still more desirably from about 20 seconds minutes to about 5 minutes.

It is generally desirable that the liquid solution containing the crosslinkable compound has a viscosity suitable for allowing sufficient mixing of the formed beads therein; that is, the viscosity of the liquid solution should not be so high that stirring and mixing is substantially impaired and the ability to keep the formed beads separated reduced. To that end, the liquid solution containing the crosslinkable compound generally contains from about 0.1% (by weight liquid solution) to about 50% (by weight liquid solution), desirably from about 0.1% (by weight liquid solution) to about 25% (by weight liquid solution) and more desirably from about 0.1% (by weight liquid solution) to about 1% (by weight liquid solution) crosslinkable compound.

Any number of crosslinkable compounds can be incorporated into the liquid solution to form the encapsulated layer around the aqueous core composition upon contact with the encapsulating activator. Some suitable crosslinkable compounds include, for example, sodium alginate, anionic dispersed latex emulsions, polyacrylic acid, polyvinyl alcohol, polyvinyl acetate, carbonates, sulfates, phosphates, borates, and combinations thereof. A particularly desirable crosslinkable compound is sodium alginate.

Once a sufficient amount of time has passed for the encapsulating layer to form on the aqueous core composition, the formed beads may be removed from the liquid including the crosslinkable compound. The resulting microencapsulated delivery vehicles may optionally be washed several times to remove any crosslinkable compound thereon and are then ready for use or for further processing. One suitable washing liquid is deionized water.

In one embodiment, the microencapsulated delivery vehicles formed as described above are subjected to a process to impart a moisture protective layer thereon that surrounds the encapsulating layer that comprises the crosslinked compound. This moisture protective layer provides the microencapsulated delivery vehicle with increased protection from water and other fluids; that is, it makes the microencapsulated delivery vehicle substantially fluid impervious and allows the microencapsulated delivery vehicle to survive long term in various products and environments and not degrade until the moisture protective layer is ruptured by mechanical action. The moisture protective layer may be a single layer applied onto the microencapsulated delivery vehicle, or may comprise several layers one on top of the other.

The moisture protective layer may be applied to the microencapsulated delivery vehicle utilizing any number of suitable processes including, for example, atomizing or dripping a moisture protective material onto the microencapsulated delivery vehicle. Additionally, a Wurster coating process may be utilized. When a solution is used to provide the moisture protective coating, the solids content of the solution is generally from about 0.1% (by weight solution) to about 70% (by weight solution), desirably from about 0.1% (by weight solution) to about 60% (by weight solution), and still more desirably from about 5% (by weight solution) to about 40% (by weight solution). Generally, the viscosity of the solution (at 25° C.) including the moisture protective material is from about 0.6 centipoise to about 10,000 centipoise, desirably from about 20 centipoise to about 400 centipoise, and still more desirably from about 20 centipoise to about 100 centipoise.

Figure 2:
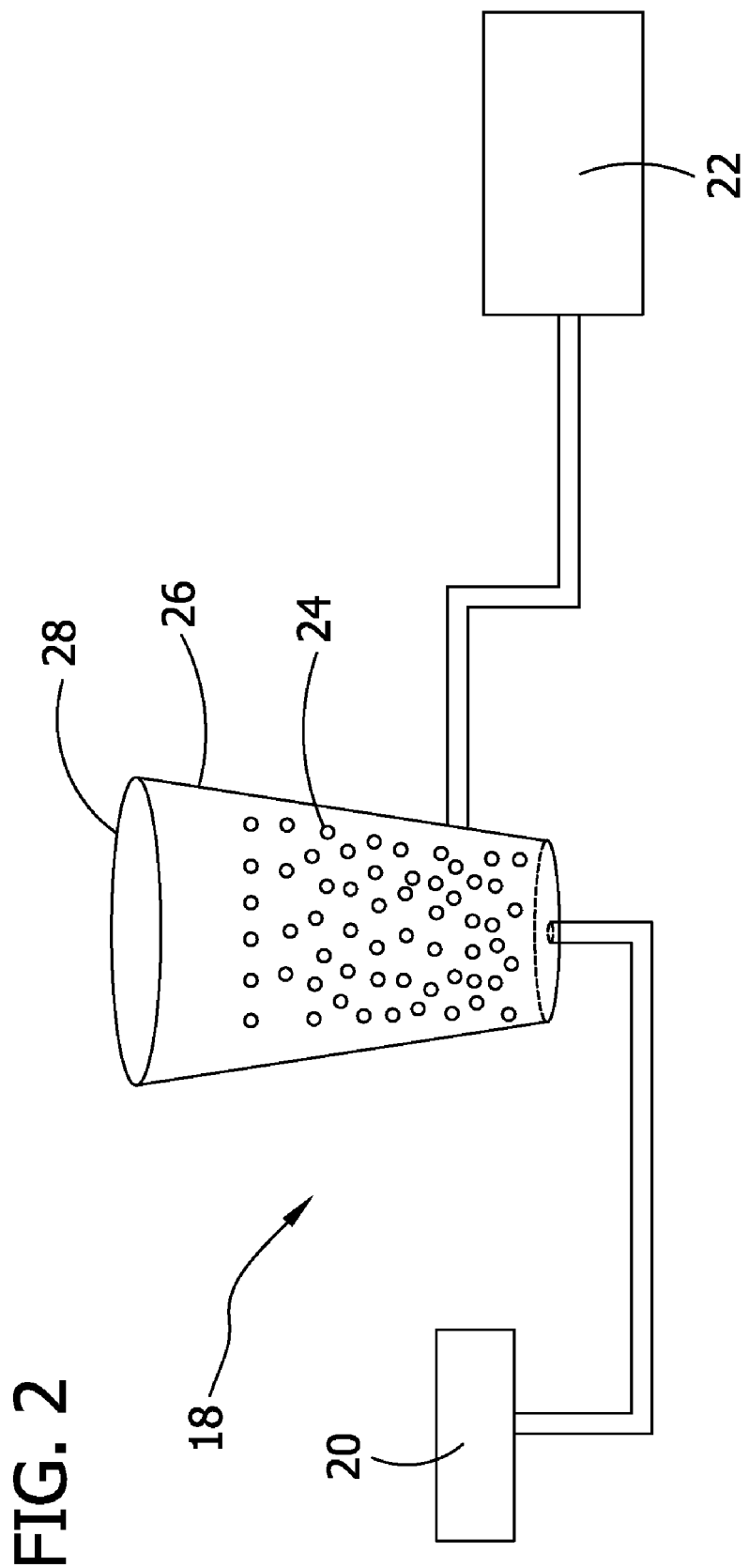
FIG. 2 depicts a fluidized bed coating apparatus for imparting a moisture protective layer to a microencapsulated delivery vehicle.

In one specific embodiment, a fluidized bed process is utilized to impart the moisture protective layer on the microencapsulated delivery vehicle. The fluidized bed is a bed or layer of microencapsulated delivery vehicles through which a stream of heated or unheated carrier gas is passed at a rate sufficient to set the microencapsulated delivery vehicles in motion and cause them to act like a fluid. As the vehicles are fluidized, a spray of a solution comprising a carrier solvent and the moisture protective material is injected into the bed and contacts the vehicles imparting the moisture protective material thereon. The treated vehicles are collected when the desired moisture protective layer thickness is achieved. The microencapsulated delivery vehicles can be subjected to one or more fluidized bed processes to impart the desired level of moisture protective layer. A suitable fluidized bed coating apparatus is illustrated in FIG. 2 wherein the fluidized bed reactor 18 includes heated carrier gas supply 20, solvent and moisture protective material supply 22, and microencapsulated delivery vehicles 24 contained in chamber 26. The heated gas and solvent exit the chamber 26 at the top 28 of chamber 26.

In another embodiment, the microencapsulated delivery vehicle, which may or may not include a moisture protective layer as described above, is subjected to a process for imparting a fugitive layer thereon surrounding the outermost layer. For example, if the microencapsulated delivery vehicle includes a moisture protective layer, the fugitive layer would be applied on the microencapsulated delivery vehicle such that it substantially completely covered the moisture protective layer. The fugitive layer can be applied in a single layer, or may be applied in multiple layers.

The fugitive layer may be applied to the microencapsulated delivery vehicle utilizing any number of suitable processes including, for example, atomizing or dripping a fugitive material onto the microencapsulated delivery vehicle. When a solution is used to provide the fugitive coating, the solids content of the solution is generally from about 1% (by weight solution) to about 70% (by weight solution), desirably from about 10% (by weight solution) to about 60% (by weight solution). The pH of the solution is generally from about 2.5 to about 11. Generally, the viscosity of the solution (at 25° C.) including the fugitive material is from about 0.6 centipoise to about 10,000 centipoise, desirably from about 20 centipoise to about 400 centipoise, and still more desirably from about 20 centipoise to about 100 centipoise. Similar to the moisture protective layer, a preferred method of applying the fugitive layer utilized a fluidized bed reactor. Also, a Wurster coating process may also be used.

In an alternative embodiment of the present disclosure, more than one active agent can be in the aqueous core composition to impart additional benefits to the end user; that is, the aqueous core composition may comprise two or more active agents. Additionally, the active agent or combination of active agents can be located in one or more of the layers surrounding the aqueous core composition including, for example, in the encapsulation layer, the moisture protective layer, and/or the fugitive layer. Also, the active agent or combination of active agents can be located in-between two of the layers on the microencapsulated delivery vehicle. For example, in one embodiment the microencapsulated delivery vehicle may include one active agent in the aqueous core composition surrounded by a crosslinked encapsulation layer surrounded by a moisture protective layer that includes therein a fragrance oil.

As noted above, the microencapsulated delivery vehicles as described herein are suitable for use in a number of products, including wipe products, wraps, such as medical wraps and bandages, headbands, wristbands, helmet pads, personal care products, cleansers, lotions, emulsions, oils, ointments, salves, balms, and the like. Additionally, other suitable products for use with the microencapsulated delivery vehicles include foods and beverage products (e.g., cereal products, frozen desserts, health drinks, meats, condiments); agricultural products (e.g., agricultural chemicals, water treatment products, animal feed, biocides, pesticides, fertilizers, pet care); and industrial products (abrasives, adhesives, automotive products, aerospace products, ceramic products, corrosion protection products, imaging products). Although described primarily herein in relation to wipes, it will be recognized by one skilled in the art that the microencapsulated delivery vehicles described herein could be incorporated into any one or more of the other products listed above.

Generally, the wipes of the present disclosure including the microencapsulated delivery vehicles can be wet wipes or dry wipes. As used herein, the term "wet wipe" means a wipe that includes greater than about 70% (by weight substrate) moisture content. As used herein, the term "dry wipe" means a wipe that includes less than about 10% (by weight substrate) moisture content. Specifically, suitable wipes for use in the present disclosure can include wet wipes, hand wipes, face wipes, cosmetic wipes, household wipes, industrial wipes, and the like. Particularly preferred wipes are wet wipes, and other wipe-types that include a solution.

Materials suitable for the substrate of the wipes are well know to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter and desirably from about 40 grams per square meter to about 90 grams per square meter.

In one particular embodiment, the wipes of the present disclosure comprise a coform basesheet of polymer fibers and absorbent fibers having a basis weight of from about 60 to about 80 grams per square meter and desirably about 75 grams per square meter. Such coform basesheets are manufactured generally as described in U.S. Pat. No. 4,100,324, issued to Anderson, et al. (Jul. 11, 1978); U.S. Pat. No. 5,284,703, issued to Everhart, et al. (Feb. 8, 1994); and U.S. Pat. No. 5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Bennettsville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

In an alternative embodiment, the wipes of the present disclosure can comprise a composite which includes multiple layers of materials. For example, the wipes may include a three layer composite which includes an elastomeric film or meltblown layer between two coform layers as described above. In such a configuration, the coform layers may define a basis weight of from about 15 grams per square meter to about 30 grams per square meter and the elastomeric layer may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

In one embodiment, the wipe is a wet wipe comprising a wetting solution in addition to the fibrous sheet material and the microencapsulated delivery vehicle. The wetting solution can be any wetting solution known to one skilled in the wet wipe art. Generally, the wetting solution can include water, emollients, surfactants, preservatives, chelating agents, pH adjusting agents, skin conditioners, fragrances, and combinations thereof. For example, one suitable wetting solution for use in the wet wipe of the present disclosure comprises about 98% (by weight) water, about 0.6% (by weight) surfactant, about 0.3% (by weight) humectant, about 0.3% (by weight) emulsifier, about 0.2% (by weight) chelating agent, about 0.35% (by weight) preservative, about 0.002% (by weight) skin conditioning agent, about 0.03% (by weight) fragrance, and about 0.07% (by weight) pH adjusting agent. One specific wetting solution suitable for use in the wet wipe of the present disclosure is described in U.S. Pat. No. 6,673,358, issued to Cole et al. (Jan. 6, 2004), which is incorporated herein by reference to the extent it is consistent herewith.

Generally, the elapsed time between the dispensing of a wipe product and use of the product is about 2 seconds or less, and typically is about 6 seconds or less. As such, once the microencapsulated delivery vehicle of the present disclosure is ruptured and its contents released, the contents of the microencapsulated delivery vehicle begin to provide a benefit that can be perceived in less than about 20 seconds. More suitably, the benefit is perceived in less than about 10 seconds, even more suitably, in less than about 5 seconds, and even more suitably, in less than about 2 seconds.

To generate the benefits described above, the wipes of the present disclosure suitably comprise from about 0.33 grams per square meter to about 500 grams per square meter microencapsulated delivery vehicle. More suitably, the wipes comprise from about 6.0 grams per square meter to about 175 grams per square meter microencapsulated delivery vehicle, even more suitably from about 16 grams per square meter to about 90 grams per square meter, and even more suitably, from about 30 grams per square meter to about 75 grams per square meter microencapsulated delivery vehicle.

The microencapsulated delivery vehicle can be applied to the wipe using any means known to one skilled in the art. Preferably, the microencapsulated delivery vehicle is embedded into the core of the fibrous sheet material of the wipe. By embedding the microencapsulated delivery vehicle into the core of the fibrous sheet material, the wipe will have a reduced grittiness feel because of a cushion effect and the ruptured shells of the microencapsulated delivery vehicle will not come into direct contact with the user's skin. Additionally, when the microencapsulated delivery vehicle is located in the core of the fibrous sheet material, the microencapsulated delivery vehicle is better protected from premature release of the active agents caused by the conditions of manufacturing, storage, and transportation of the wipe.

In one embodiment, the microencapsulated delivery vehicle is embedded inside of the fibrous sheet material. For example, in one specific embodiment, the fibrous sheet material is one or more meltblown layers made by providing a stream of extruded molten polymeric fibers. To incorporate the microencapsulated delivery vehicles, a stream of microencapsulated delivery vehicles can be merged with the stream of extruded molten polymeric fibers and collected on a forming surface such as a forming belt or forming drum to form the wipe comprising the microencapsulated delivery vehicle. Optionally, a forming layer can be placed on the forming surface and used to collect the microencapsulated delivery vehicles in the wipe. By using this method, the microencapsulated delivery vehicle is mechanically entrapped within the forming layer.

The stream of meltblown polymeric fibers may be provided by meltblowing a copolymer resin or other polymer. For example, in one embodiment, the melt temperature for a copolymer resin such as Vistamaxx® PLTD 1810 can be from about 450° F. (232° C.) to about 540° F. (282° C.). As noted above, suitable techniques for producing nonwoven fibrous webs, which include meltblown fibers, are described in the previously incorporated U.S. Pat. Nos. 4,100,324 and 5,350,624. The meltblowing techniques can be readily adjusted in accordance with the knowledge of one skilled in the art to provide turbulent flows that can operatively intermix the fibers and the microencapsulated delivery vehicles. For example, the primary air pressure may be set at 5 pounds per square inch (psi) and the meltblown nozzles may be 0.020 inch spinneret hole nozzles.

Additionally, immediately following the formation of the meltblown structure, the meltblown polymeric fibers can be tacky, which can be adjusted to provide additional adhesiveness between the fibers and the microencapsulated delivery vehicles.

In another embodiment, the fibrous sheet material is a coform basesheet comprising a matrix of thermoplastic polymeric meltblown fibers and absorbent cellulosic fibers. Similar to the meltblown embodiment above, when the fibrous sheet material is a matrix of thermoplastic polymeric meltblown fibers and absorbent cellulosic fibers, a stream of microencapsulated delivery vehicles can be merged with a stream of cellulosic fibers and a stream of polymeric fibers into a single stream and collected on a forming surface such as a forming belt or forming drum to form a wipe comprising a fibrous sheet material with the microencapsulated delivery vehicles within its core.

The stream of absorbent cellulosic fibers may be provided by feeding a pulp sheet into a fiberizer, hammermill, or similar device as is known in the art. Suitable fiberizers are available from Hollingsworth (Greenville, S.C.) and are described in U.S. Pat. No. 4,375,448, issued to Appel, et al. (Mar. 1, 1983), which is incorporated by reference to the extent to which it is consistent herewith. The stream of polymeric fibers can be provided as described above.

The thickness of the fibrous sheet material will typically depend upon the diameter size of the microencapsulated delivery vehicle, the fibrous sheet material basis weight, and the microencapsulated delivery vehicle loading. For example, as the size of the microencapsulated delivery vehicle is increased, the fibrous sheet material must be thicker to prevent the wipe from having a gritty feel.

In another embodiment, the fibrous sheet material is made up of more than one layer. For example, when the fibrous sheet material is a meltblown material, the fibrous sheet material can suitably be made up of two meltblown layers secured together, more suitably three meltblown layers, even more suitably four meltblown layers, and even more suitably five or more meltblown layers. When the fibrous sheet material is a coform basesheet, the fibrous sheet material can suitably be made up of two coform basesheet layers secured together, more suitably three coform basesheet layers, even more suitably four coform basesheet layers, even more suitably five or more coform basesheet layers. Moreover, when the fibrous sheet material includes a film, the fibrous sheet material can suitably be made up of two film layers, more suitably three film layers, even more suitably four film layers, and even more suitably five or more film layers. In one embodiment, the layers are separate layers. In another embodiment, the layers are plied together.

Using the additional layers will allow for improved capture of the microencapsulated delivery vehicle. This helps to ensure the microencapsulated delivery vehicle will remain in the wipe during shipping and storage. Additionally, as the microencapsulated delivery vehicle becomes further entrapped in the fibrous sheet material, the grittiness of the wipe is reduced.

To incorporate the microencapsulated delivery vehicle in between the layers of fibrous sheet material, the microencapsulated delivery vehicle is sandwiched between a first layer and a second layer of the fibrous sheet material, and the layers are then laminated together using any means known in the art. For example, the layers can be secured together thermally or by a suitable laminating adhesive composition.

Thermal bonding includes continuous or discontinuous bonding using a heated roll. Point bonding is one suitable example of such a technique. Thermal bonds should also be understood to include various ultrasonic, microwave, and other bonding methods wherein the heat is generated in the non-woven or the film.

In a preferred embodiment, the first layer and second layer are laminated together using a water insoluble adhesive composition. Suitable water insoluble adhesive compositions can include hot melt adhesives and latex adhesives as described in U.S. Pat. No. 6,550,633, issued to Huang, et al. (Apr. 22, 2003); U.S. Pat. No. 6,838,154, issued to Anderson, et al. (Oct. 25, 2005); and U.S. Pat. No. 6,958,103, issued to Varona et al. (Jan. 4, 2005), which are hereby incorporated by reference to the extent they are consistent herewith. Suitable hot melt adhesives can include, for example, RT 2730 APAO and RT 2715 APAO, which are amorphous polyalphaolefin adhesives (commercially available from Huntsman Polymers Corporation, Odessa, Tex.) and H2800, H2727A, and H2525A, which are all styrenic block copolymers (commercially available from Bostik Findley, Inc., Wauwatosa, Wis.). Suitable latex adhesives include, for example, DUR-O-SET E-200 (commercially available from National Starch and Chemical Co., Ltd., Bridgewater, N.J.) and Hycar 26684 (commercially available from B. F. Goodrich, Laval, Quebec).

The water insoluble adhesive composition can additionally be used in combination with the microencapsulated delivery vehicle between the first and second layers of the fibrous sheet material. The water insoluble adhesive composition will provide improved binding of the microencapsulated delivery vehicle to the first and second layers of the fibrous sheet material. Typically, the adhesive composition can be applied to the desired area by spraying, knifing, roller coating, or any other means suitable in the art for applying adhesive compositions.

Suitably, the adhesive composition can be applied to the desired area of the wipe in an amount of from about 0.01 grams per square meter to about 20 grams per square meter. More suitably, the adhesive composition can be applied in an amount of from about 0.05 grams per square meter to about 0.5 grams per square meter.

In yet another embodiment, the microencapsulated delivery vehicle may be distributed within a pocket of the fibrous sheet material. Similar to the pattern distribution method described herein below, the pockets of microencapsulated delivery vehicles provide for a targeted benefit sensation in the wipe.

As an alternative to embedding the microencapsulated delivery vehicles into the core of the fibrous sheet material, the microencapsulated delivery vehicles can be deposited on the outer surface of the fibrous sheet material. In one embodiment, the microencapsulated delivery vehicles are deposited on one outer surface of the fibrous sheet material. In another embodiment, the microencapsulated delivery vehicles are deposited on both outer surfaces of the fibrous sheet material.

To provide for better attachment of the microencapsulated delivery vehicles to the outer surface of the fibrous sheet material, a water insoluble adhesive composition can be applied with the microencapsulated delivery vehicles onto the outer surface of the fibrous sheet material. Suitable water insoluble adhesive compositions are described herein above. Suitably, the adhesive composition can be applied to the outer surface of the fibrous sheet material in an amount of from about 0.01 grams per square meter to about 20 grams per square meter. More suitably, the adhesive composition can be applied in an amount of from about 0.05 grams per square meter to about 0.5 grams per square meter.

The microencapsulated delivery vehicles may be embedded in or distributed on the fibrous sheet material in a continuous layer or a patterned layer. By using a patterned layer, a targeted benefit sensation can be achieved. These methods of distribution can additionally reduce manufacturing costs as reduced amounts of microencapsulated delivery vehicles are required. Suitably, the microencapsulated delivery vehicles can be distributed in patterns including, for example, characters, an array of separate lines, swirls, numbers, or dots of microencapsulated delivery vehicles. Continuous patterns, such as stripes or separate lines that run parallel with the machine direction of the web, are particularly preferred as these patterns may be more process-friendly.

Additionally, the microencapsulated delivery vehicles may be colored using a coloring agent prior to applying the microencapsulated delivery vehicles to the fibrous sheet material. The coloring of the microencapsulated delivery vehicles can improve the aesthetics of the wipe. Additionally, in embodiments where targeted benefits are desired, the coloring of the microencapsulated delivery vehicles can direct the consumer of the wipe product to the location of the microencapsulated delivery vehicles in the wipe.

Suitable coloring agents include, for example, dyes, color additives, and pigments or lakes. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin. Also, many dyes found suitable for use in the European Union and in Japan may be suitable for use as coloring agents in the present disclosure.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

Any means known to one of skill in the art capable of producing sufficient force to break the capsules can be used in the present disclosure. In one embodiment, the microencapsulated delivery vehicles can be broken by the user at the point of dispensing the wipe from a package. For example, a mechanical device located inside of the package containing the wipes can produce a rupture force sufficient to rupture the capsules upon dispensing the wipe, thereby exposing the contents of the microencapsulated delivery vehicles.

In another embodiment, the capsules can be broken by the user just prior to or at the point of use of the wipe. By way of example, in one embodiment, the force produced by the hands of the user of the wipe can break the capsules, exposing the contents of the microencapsulated delivery vehicles.

The present disclosure is illustrated by the following examples which are merely for the purpose of illustration and are not to be regarded as limiting the scope of the disclosure or manner in which it may be practiced.

EXAMPLE 1

In this example, samples of microencapsulated delivery vehicles incorporating calcium chloride within an aqueous core composition containing water were prepared. The integrity of the samples was then evaluated after a two-week storage period.

To prepare each sample, 25.0 grams of calcium chloride (commercially available from Sigma-Aldrich, St. Louis, Mo.) was added to 70.0 grams deionized water. Three grams of ITC Pretested gum (commercially available from TIC Gums, Belcamp, Md.) were then added to the 90.0 grams of 26% (by weight) calcium chloride solution to increase the solution's viscosity. This core composition was then dripped into a 0.5% (by weight) sodium alginate DBM solution (available from ISP Technologies) using an eyedropper and allowed to stand in the alginate solution for approximately one minute to allow for encapsulation of the aqueous core composition to produce a microencapsulated delivery vehicle. The microencapsulated delivery vehicle was thoroughly rinsed with tap water.

The microencapsulated delivery vehicles were approximately one to eight millimeters in diameter. The vehicles were stored in a plastic bag for two weeks. After two weeks, the vehicles were found to have maintained their size and shape.

EXAMPLE 2

In this example, samples of microencapsulated delivery vehicles incorporating calcium chloride within a frozen aqueous core composition containing water (i.e., ice) were prepared. The integrity of the samples were then evaluated after a two-week storage period.

To prepare each sample, 25.0 grams of calcium chloride (commercially available from Sigma-Aldrich, St. Louis, Mo.) was added to 70.0 grams deionized water. Using an eyedropper, the 26% (by weight) calcium chloride solution was dripped into liquid nitrogen to freeze the matrix material (i.e., calcium chloride solution) within the core composition. Individual frozen beads of aqueous core composition were carefully removed and immediately dropped into a 0.5% (by weight) sodium alginate DBM solution (available from ISP Technologies) at room temperature. The alginate solution was slightly agitated with a magnetic stir bar. The microencapsulated delivery vehicles were removed from the solution after about 30 seconds to about one minute. The microencapsulated delivery vehicles were thoroughly rinsed with tap water.

The microencapsulated delivery vehicles were approximately one to five millimeters in diameter. The vehicles were stored in a plastic bag for two weeks. After two weeks, the vehicles were found to have maintained their size and shape.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A microencapsulated delivery vehicle comprising an aqueous core composition surrounded by an encapsulation layer, the aqueous core composition comprising an encapsulating activator, a matrix material, and an active agent, wherein the active agent is surrounded by a hydrophobic wax material and wherein the microencapsulated delivery vehicle has a diameter of from about 5 micrometers to about 5000 micrometers.

2. The microencapsulated delivery vehicle as set forth in claim 1 wherein the aqueous core composition is present in the microencapsulated delivery vehicle in an amount of from about 1% (by weight microencapsulated delivery vehicle) to about 99.99% (by weight microencapsulated delivery vehicle).

3. The microencapsulated delivery vehicle as set forth in claim 1 wherein the matrix material is water.

4. The microencapsulated delivery vehicle as set forth in claim 3 wherein the water is present in the aqueous core composition in an amount of from about 60% (by weight aqueous core composition) to about 98% (by weight aqueous core composition).

5. The microencapsulated delivery vehicle as set forth in claim 3 wherein the aqueous core composition further comprises a viscosity increasing agent.

6. The microencapsulated delivery vehicle as set forth in claim 5 wherein the aqueous core composition has a yield stress of at least about 5 Pa.

7. A substantially fluid-impervious microencapsulated delivery vehicle comprising an aqueous core composition, an encapsulation layer surrounding the aqueous core composition, and a moisture protective layer surrounding the encapsulation layer, wherein the aqueous core composition comprises an encapsulating activator, a matrix material, and an active agent, wherein the active agent is surrounded by a hydrophobic wax material and wherein the microencapsulated delivery vehicle has a diameter of from about 5 micrometers to about 5000 micrometers.

8. The substantially fluid-impervious microencapsulated delivery vehicle as set forth in claim 7 wherein the aqueous core composition is present in the microencapsulated delivery vehicle in an amount of from about 20% (by weight microencapsulated delivery vehicle) to about 70% (by weight microencapsulated delivery vehicle).

9. The substantially fluid-impervious microencapsulated delivery vehicle as set forth in claim 7 wherein the aqueous core composition further comprises a viscosity increasing agent.

10. The substantially fluid-impervious microencapsulated delivery vehicle as set forth in claim 9 wherein the aqueous core composition has a yield stress of at least about 5 Pa.

11. A stabilized microencapsulated delivery vehicle comprising an aqueous core composition, an encapsulation layer surrounding the aqueous core composition, and a fugitive layer surrounding the encapsulation layer, wherein the aqueous core composition comprises an encapsulating activator, a matrix material, and an active agent, wherein the active agent is surrounded by a hydrophobic wax material and wherein the microencapsulated delivery vehicle has a diameter of from about 5 micrometers to about 5000 micrometers.

12. The stabilized microencapsulated delivery vehicle as set forth in claim 11 wherein the fugitive layer is comprised of a material selected from the group consisting of polymers of dextrose, sugars, starches, alginate, acrylates, polyvinyl alcohol, gum arabic, polyacrylamide, hydroxypropyl cellulose, hydroxypropyl methylcellulose, polyvinyl pyrrolidone, poly(2-acrylamido-2-methyl-1-propanesulfonic acid), poly(acrylamido-N-propyltrimethylammonium chloride), and combinations thereof.

13. The stabilized microencapsulated delivery vehicle as set forth in claim 11 wherein the aqueous core composition is present in the microencapsulated delivery vehicle in an amount of from about 20% (by weight microencapsulated delivery vehicle) to about 70% (by weight microencapsulated delivery vehicle).

14. The stabilized microencapsulated delivery vehicle as set forth in claim 11 wherein the matrix material is water.

15. The stabilized microencapsulated delivery vehicle as set forth in claim 14 wherein the aqueous core composition further comprises a viscosity increasing agent.

16. The stabilized microencapsulated delivery vehicle as set forth in claim 15 wherein the aqueous core composition has a yield stress of at least about 5 Pa.

17. A microencapsulated delivery vehicle comprising an aqueous core composition surrounded by an encapsulation layer, the aqueous core composition comprising an encapsulating activator, a matrix material, and a heating agent, wherein the heating agent is surrounded by a hydrophobic wax material and wherein the microencapsulated delivery vehicle has a diameter of from about 5 micrometers to about 5000 micrometers.

18. The microencapsulated delivery vehicle as set forth in claim 17 wherein the aqueous core composition is present in the microencapsulated delivery vehicle in an amount of from about 1% (by weight microencapsulated delivery vehicle) to about 99.99% (by weight microencapsulated delivery vehicle).

19. The microencapsulated delivery vehicle as set forth in claim 17 wherein the aqueous core composition further comprises a viscosity increasing agent.

20. The microencapsulated delivery vehicle as set forth in claim 19 wherein the aqueous core composition has a yield stress of at least about 5 Pa.

* * * * *

UNITED STATES PATENT AND TRADEMARK OFFICE
CERTIFICATE OF CORRECTION

PATENT NO. : 8,192,841 B2
APPLICATION NO. : 11/610980
DATED : June 5, 2012
INVENTOR(S) : John David Amundson et al.

It is certified that error appears in the above-identified patent and that said Letters Patent is hereby corrected as shown below:

In the Specification

In Column 10, Line 38, delete "*Pyrus cyclonia*" and insert -- *Pyrus cydonia* -- therefor.

Signed and Sealed this
Twelfth Day of May, 2015

Michelle K. Lee
*Director of the United States Patent and Trademark Office*